US007109371B2

(12) United States Patent
Clissold et al.

(10) Patent No.: US 7,109,371 B2
(45) Date of Patent: Sep. 19, 2006

(54) PROSTAGLANDIN SYNTHESIS

(75) Inventors: Derek Wyndham Clissold, Wokingham (GB); Stuart Wilbert Craig, Lowell, MA (US); Rajendrakumar Reddy Gadikota, Lowell, MA (US); Min He, Ayer, MA (US); Jurjus Fayez Jurayj, Acton, MA (US); Shahrokh Kazerani, Leominster, MA (US); Erwin Rannala, Hants (GB); Pradeep Kumar Sharma, Westford, MA (US)

(73) Assignee: Johnson Matthey Public Limited Company, London (GB)

( * ) Notice: Subject to any disclaimer, the term of this patent is extended or adjusted under 35 U.S.C. 154(b) by 37 days.

(21) Appl. No.: 10/751,611

(22) Filed: Jan. 5, 2004

(65) Prior Publication Data

US 2005/0154220 A1    Jul. 14, 2005

(51) Int. Cl.
C07C 69/73    (2006.01)
C07C 69/66    (2006.01)
C07C 231/00   (2006.01)
C07C 45/00    (2006.01)
C07D 307/87   (2006.01)

(52) U.S. Cl. .................. 560/183; 560/188; 564/134; 564/139; 568/361; 568/445; 568/670; 568/838; 549/462

(58) Field of Classification Search ............... 560/183, 560/188; 564/134, 139; 568/361, 445, 670, 568/838; 549/462
See application file for complete search history.

(56) References Cited

U.S. PATENT DOCUMENTS

| 3,920,723 | A | | 11/1975 | Nelson |
| 3,931,279 | A | * | 1/1976 | Nelson .................. 260/468 |
| 4,504,417 | A | | 3/1985 | Floyd, Jr. et al. |
| 5,223,537 | A | * | 6/1993 | Stjernschantz et al. ..... 514/530 |
| 5,359,095 | A | * | 10/1994 | Resul .................. 549/305 |
| 5,688,819 | A | * | 11/1997 | Woodward et al. ......... 514/537 |
| 5,698,733 | A | | 12/1997 | Hellberg et al. |
| 6,689,901 | B1 | * | 2/2004 | Henegar .................. 562/465 |
| 2003/0187071 | A1 | | 10/2003 | Henegar |

FOREIGN PATENT DOCUMENTS

| EP | 0 178 139 A3 | 4/1986 |
| GB | 1 501 864 | 2/1978 |
| GB | 1 582 853 | 1/1981 |
| JP | 57-171965 | 10/1982 |
| JP | 59-44336 | 3/1984 |
| JP | 60-166639 | 8/1985 |
| JP | 1-228933 | 9/1989 |
| WO | WO-02/090324 | 11/2002 |
| WO | WO-02/096868 | 12/2002 |
| WO | WO-02/096868 A3 | 12/2002 |

OTHER PUBLICATIONS

Paul W. Collins and Stevan W. Djuric, "Synthesis of Therapeutically Useful Prostaglandin and Prostacyclin Analogs," *Chem. Rev.*, 1993, vol. 4, pp. 1533-1564.
Chen Jianxing, Chen Hailin, and Chen Liangkang, "Synthesis of the Antiglaucoma Drug Latanoprost and its Effect on Reduction of Intraocular Pressure (IOP)," *Chinese Journal of Medicinal Chemistry*, Sep. 1988, vol. 8, No. 3, pp. 213-217.
British Search Report dated May 4, 2004, from British Appl. No. 0329379.2.
Robert Selliah et al., "Synthesis of [Phenyl-2-$^3$H]-travoprost: Isopropyl Ester Prodrug of a Selective Prostaglandin FP Receptor Agonist," *Journal of Labelled Compounds and Radiopharmaceuticals*, 2001, vol. 44, pp. 173-183.
Hisao Nakai et al., "Synthesis of 5-Fluoro-Prostaglandins," *Chemistry Letters*, 1979, pp. 1499-1502.
John C. Sih et al., "Synthesis of the Four Isomers of 5-Hydroxy $PGI_1$," *Prostaglandins*, 1978, vol. 15, No. 3, pp. 409-421.
Zuyun Cai et al., "Synthesis fo Aromatic Modified Prostaglandins from $PGA_2$," *J. Chem. Soc. Perkin Trans. I*, 1983, vol. 7, pp. 1573-15578.

(Continued)

*Primary Examiner*—Sikarl A. Witherspoon
(74) *Attorney, Agent, or Firm*—RatnerPrestia

(57) ABSTRACT

A process for the preparation of prostaglandin compounds having the formula (I):

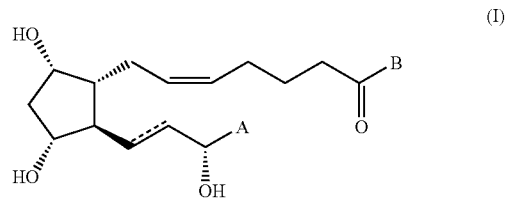

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_n OR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR" and NHR" wherein R" is $C_1$–$C_6$ alkyl groups; and

----- represents a double bond or a single bond, is disclosed. Novel intermediates are also disclosed.

48 Claims, No Drawings

OTHER PUBLICATIONS

Hazato et al., "Synthesis of Thiaprostaglandin $E_1$ Derivatives," *Chem. Pharm. Bull.*, vol. 33, No. 5, 1985, pp. 1815-1825.

Fox et al., "An Enantioconvergent Synthesis of (R)-4-Aryloxy-1-butyne-3-ols for Prostanoid Side Chains," *Adv. Synth. Catal.*, vol. 344, No. 1, 2002, pp. 50 - 56.

Maruyama et al., "Design and Synthesis of a Selective EP4-Receptor Agonist. Part 1: Discovery of 3,7-DithiaPGE$_1$ Derivatives and Identification of Their ω Chains," *Bioorganic & Medicinal Chemistry*, vol. 10, 2002, pp. 975-988.

* cited by examiner

PROSTAGLANDIN SYNTHESIS

FIELD OF THE INVENTION

The present invention relates to a novel process for the synthesis of prostaglandins and prostaglandin analogues. The present invention further relates to novel synthetic intermediates that can be used in the synthesis of prostaglandins and prostaglandin analogues.

BACKGROUND OF THE INVENTION

PGF$_\alpha$ prostaglandins and prostaglandin analogues comprise a cyclopentyl ring carrying two hydroxyl groups in a cis configuration and two side chains in a trans configuration. The side chains may contain double bonds and a variety of substituents. They have a number of therapeutic uses, e.g. for the treatment of glaucoma and ocular hypertension or to induce and accelerate labour.

A variety of methods of synthesising PGFα prostaglandins and prostaglandin analogues are known and are disclosed in, e.g. Chem. Rev. (1993, vol. 93, pages 1533–1564), WO 02/096868, WO 02/090324 and Chinese Journal of Medicinal Chemistry (1998, vol. 36, pages 213–217).

SUMMARY OF THE INVENTION

In one aspect, the invention is a process for the preparation of a compound of formula (VIII):

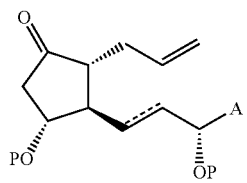
(VIII)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_n OR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; P is a hydroxyl protecting group; and

----- represents a double bond or a single bond;
comprising converting a compound of formula (IX):

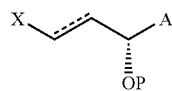
(IX)

wherein A, P and

----- are as defined above and X is a leaving group, to a cuprate reagent and performing a 1,4 addition reaction between the cuprate reagent and a compound of formula (X):

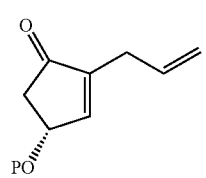
(X)

wherein P is as defined above.

In another aspect, the invention is a compound of formula (VIII) as defined above.

In yet another aspect, the invention is a process for the preparation of a compound of formula (VIIa):

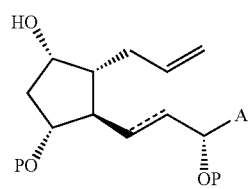
(VIIa)

comprising selectively reducing a compound of formula (VIII):

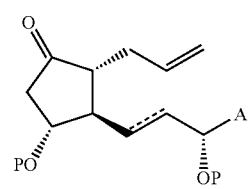
(VIII)

wherein A, P and

----- are as defined above.

In still another aspect, the invention is a compound of formula VIIa as described above.

In a further aspect, the invention is a process for the preparation of a compound of formula (VIIb):

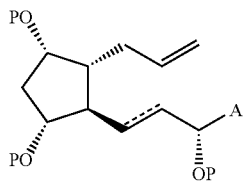
(VIIb)

comprising protecting a compound of formula (VIIa):

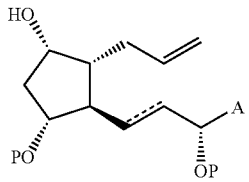
(VIIa)

wherein A, P and

----- are as defined above, with a hydroxyl protecting group.

In a yet further aspect, the invention is the compound of formula (VIIb) as described above.

In a still further aspect, the invention is a process for the preparation of a compound of formula (VIIc):

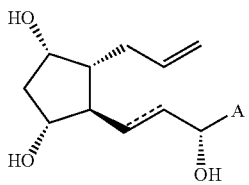
(VIIc)

comprising deprotecting a compound of formula (VIIa):

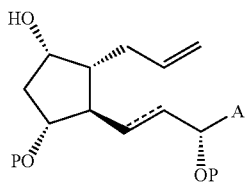
(VIIa)

wherein A, P and

----- are as defined above.

In an even further aspect, the invention is a compound of formula (VIIc) as described above.

In another aspect, the invention is a process for the preparation of a compound of formula (VIa), (VIb), (VIc), (Va), (Vb) or (Vc):

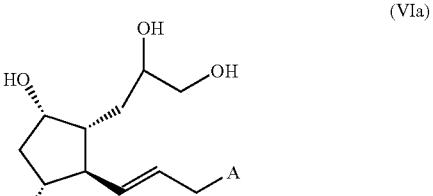
(VIa)

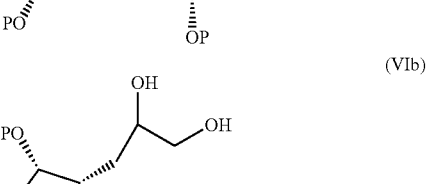
(VIb)

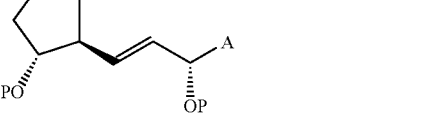
(VIc)

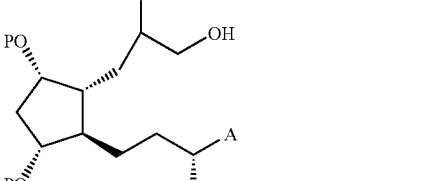
(Va)

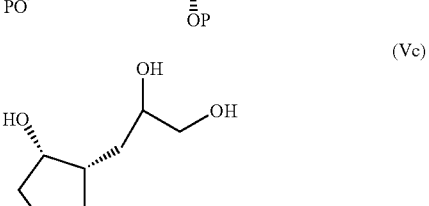
(Vb)

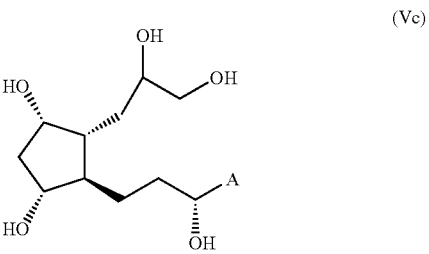
(Vc)

comprising dihydroxylating a compound of formula (VIIa), a compound of formula (VIIb) or a compound of formula (VIIc):

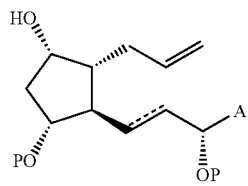

(VIIa)

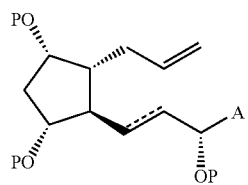

(VIIb)

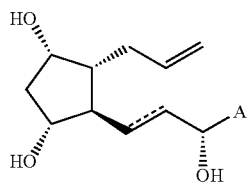

(VIIc)

wherein A and P and

----- are as defined above.

In yet another aspect, the invention is a compound of formula (VIa), (VIb), (VIc), (Va), (Vb) or (Vc) as described above.

In still another aspect, the invention is a process for the preparation of a compound of formula (Va), (Vb) or (Vc):

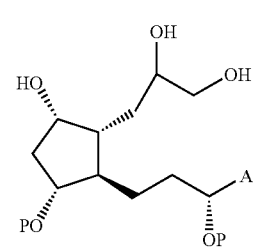

(Va)

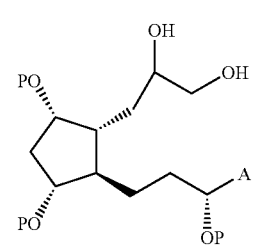

(Vb)

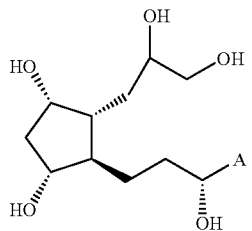

(Vc)

comprising reducing a double bond of a compound of formula (VIa), a compound of formula (VIb) or a compound of formula (VIc):

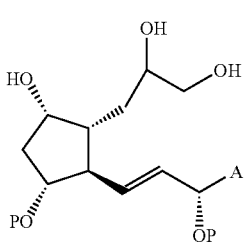

(VIa)

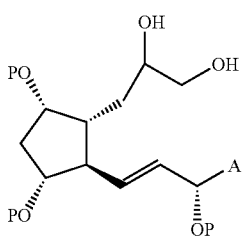

(VIb)

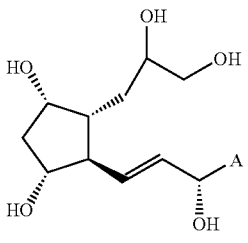

(VIc)

wherein A and P are as defined above.

In a further aspect, the invention is a process for the preparation of a compound of formula (IVa), (IVb) or (IVc):

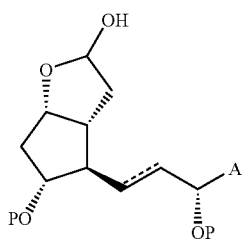

(IVa)

-continued

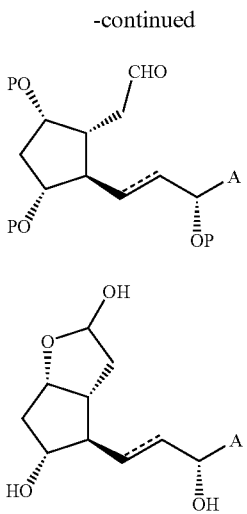
(IVb)

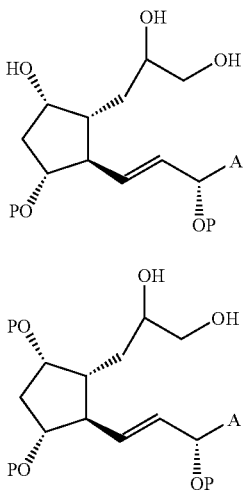
(IVc)

comprising performing a diol cleavage reaction on a compound of formula (VIa), (Va), (VIb), (Vb), (VIc) or (Vc):

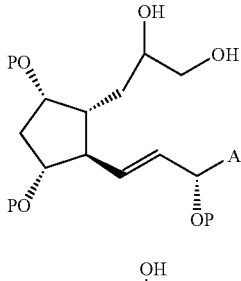
(VIa)

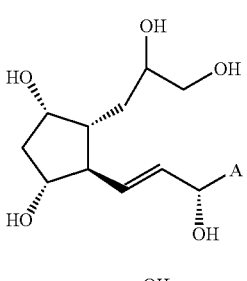
(VIb)

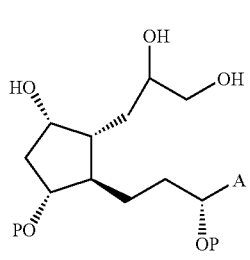
(VIc)

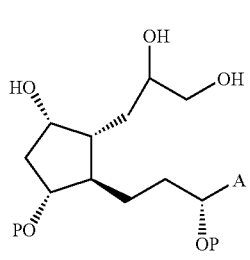
(Va)

-continued

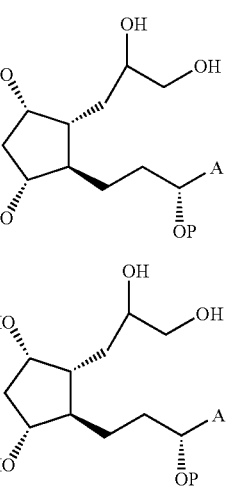
(Vb)

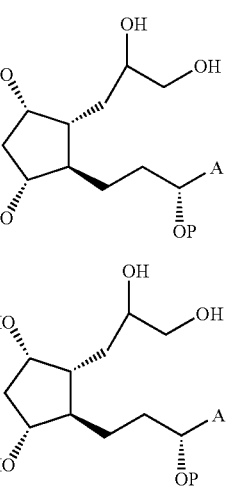
(Vc)

wherein A and P and

─ ─ ─ ─ ─ are as defined above.

In a still further aspect, the invention is a compound having the formula (14):

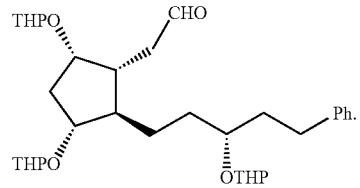
(14)

In a yet further aspect, the invention is a process for synthesising Latanoprost comprising the steps of:

a) preparing a compound of formula (3):

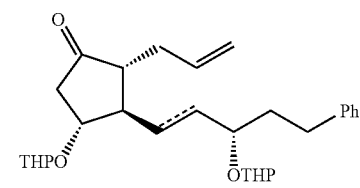
(3)

said preparing comprising converting a compound of formula (1):

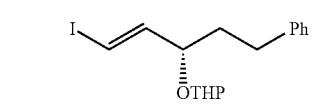
(1)

to a cuprate reagent and performing a 1,4 addition reaction between the cuprate reagent and a compound of formula (2):

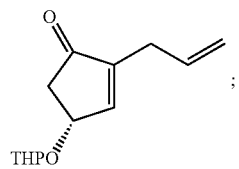
(2)

b) selectively reducing the compound of formula (3) to provide a compound of formula (4):

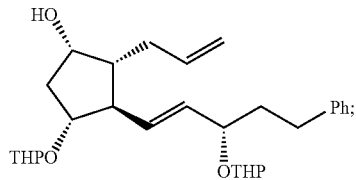
(4)

c) dihydroxylating the compound of formula (4) to provide a compound of formula (7):

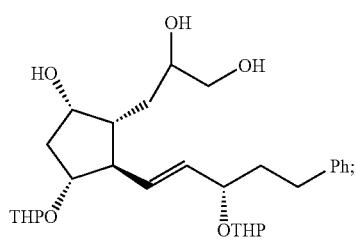
(7)

d) reducing the compound of formula (7) to provide a compound of formula (10):

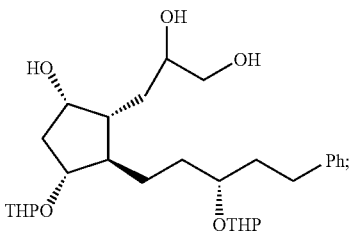
(10)

e) performing a diol cleavage reaction on the compound of formula (10) to provide a compound formula (13):

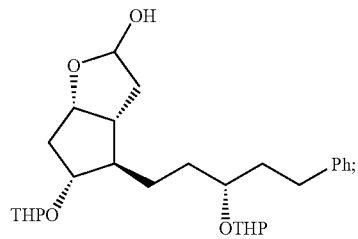
(13)

f) performing a Wittig reaction on the compound of formula (13) to provide a compound of formula (16):

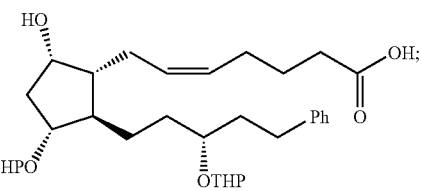
(16)

g) esterifying the compound of formula (16) to provide a compound of formula (19):

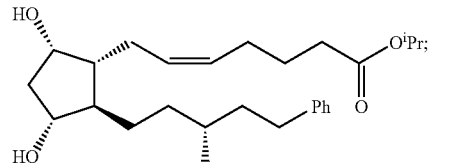
(19)

and h) deprotecting the compound of formula (19) to provide Latanoprost.

In another aspect, the invention is a process for synthesising Latanoprost comprising the steps of:

a) preparing a compound of formula (3):

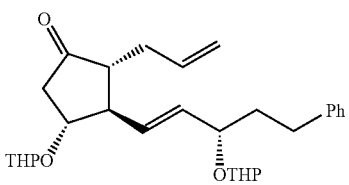
(3)

said preparing comprising converting a compound of formula (1):

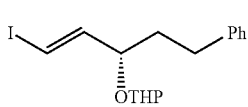
(1)

to a cuprate reagent and performing a 1,4 addition reaction between the cuprate reagent and a compound of formula (2):

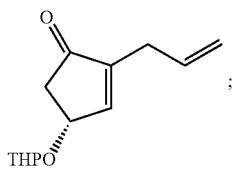
(2)

b) selectively reducing the compound of formula (3) to provide a compound of formula (4):

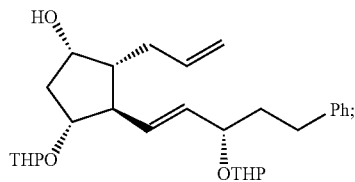
(4)

c) protecting the compound of formula (4) to provide a compound of formula (5):

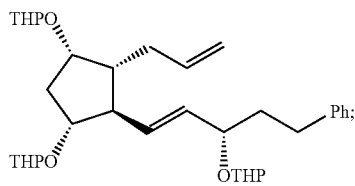
(5)

d) dihydroxylating the compound of formula (5) to provide a compound of formula (8):

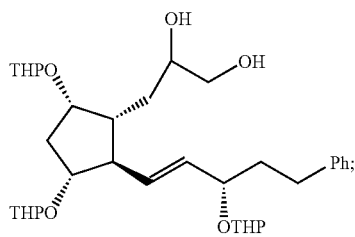
(8)

e) reducing the compound of formula (8) to provide a compound of formula (11):

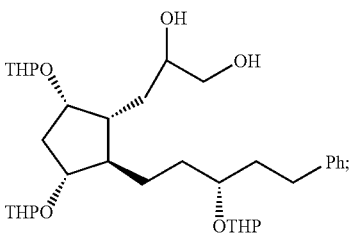
(11)

f) performing a diol cleavage reaction on the compound of formula (11) to provide a compound of formula (14):

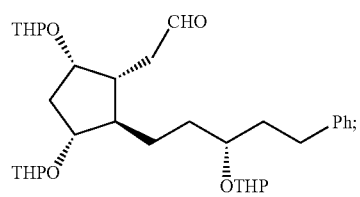
(14)

g) performing a Witting reaction on the compound of formula (14) to provide a compound of formula (17):

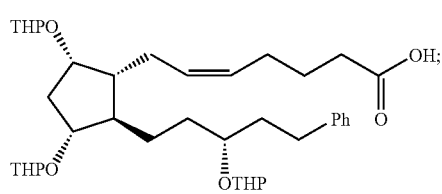
(17)

h) esterifying the compound of formula (17) to provide a compound of formula (20):

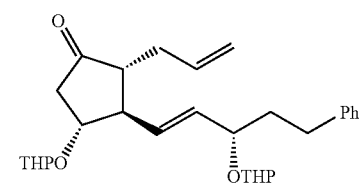
(20)

i) deprotecting the compound of formula (20) to provide Latanoprost.

In another aspect, the invention is a process for synthesising Latanoprost comprising the steps of:

a) preparing a compound of formula (3):

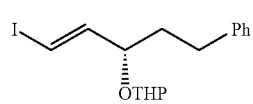
(3)

said preparing comprising converting a compound of formula (1):

(1)

to a cuprate reagent and performing a 1,4 addition reaction between the cuprate reagent and a compound of formula (2):

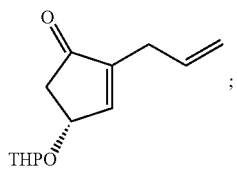
(2)

b) selectively reducing the compound of formula (3) to provide a compound of formula (4):

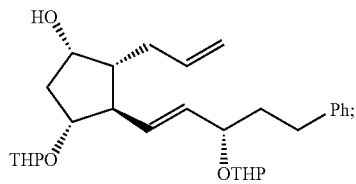
(4)

c) deprotecting the compound of formula (4) to provide a compound of formula (6):

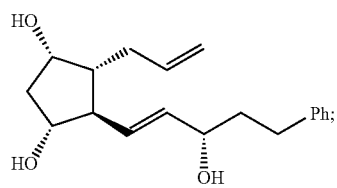
(6)

d) dihydroxylating the compound of formula (6) to provide a compound of formula (9):

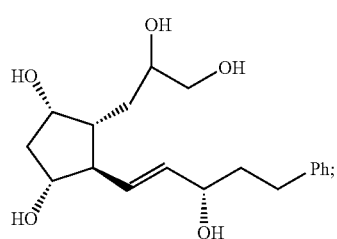
(9)

e) reducing the compound of formula (9) to provide a compound of formula (12):

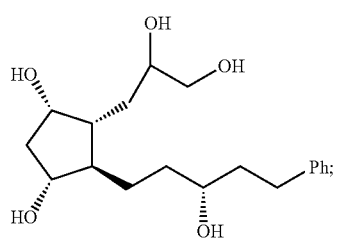
(12)

f) performing a diol cleavage reaction on the compound of formula (12) to provide a compound of formula (15):

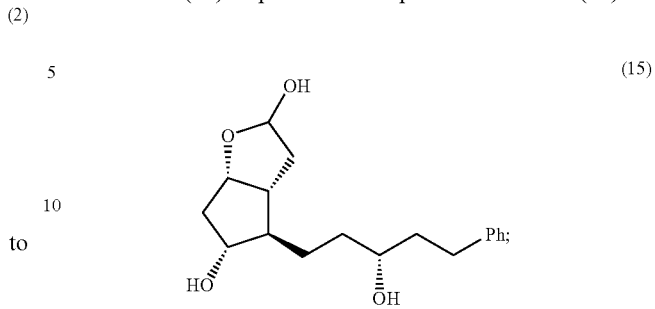
(15)

g) performing a Wittig reaction on the compound of formula (15) to provide a compound of formula (18):

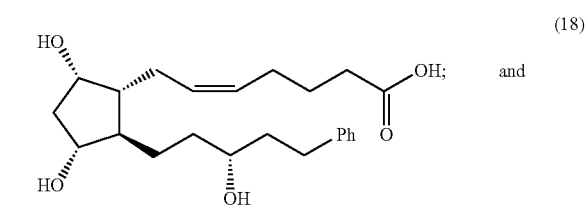
(18) and h) esterifying the compound of formula (18) to provide Latanoprost.

In another aspect, the invention is a process for synthesising Bimatoprost comprising the steps of:

a) preparing a compound of formula (3):

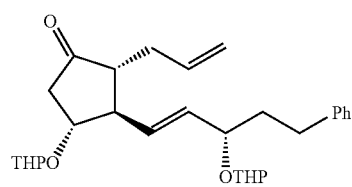
(3)

said preparing comprising converting a compound of formula (1):

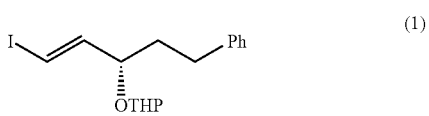
(1)

to a cuprate reagent and performing a 1,4 addition reaction between the cuprate reagent and a compound of formula (2):

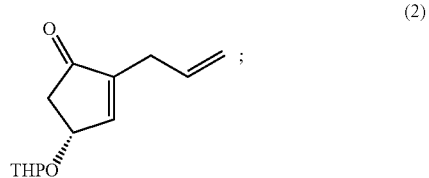
(2)

b) selectively reducing the compound of formula (3) to provide a compound of formula (4):

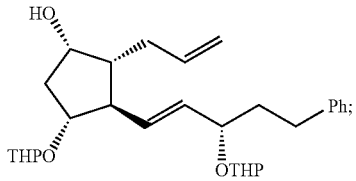
(4)

c) dihydroxylating the compound of formula (4) to provide a compound of formula (7):

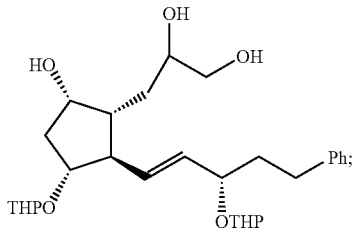
(7)

d) performing a diol cleavage reaction on the compound of formula (7) to provide a compound of formula (23):

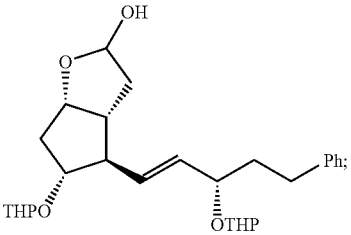
(23)

e) performing a Wittig reaction on the compound of formula (23) to provide a compound of formula (26):

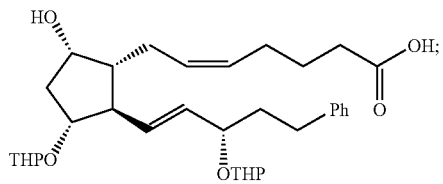
(26)

f) amidating the compound of formula (26) to provide a compound of formula (29):

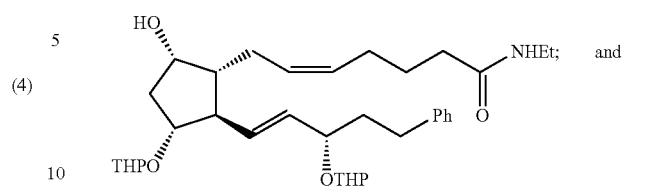
(29)

g) deprotecting the compound of formula (29) to provide Bimatoprost.

In another aspect, the invention is a process for synthesising Bimatoprost comprising the steps of:

a) preparing a compound of formula (3):

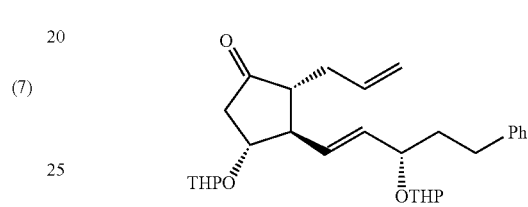
(3)

said preparing comprising converting a compound of formula (1):

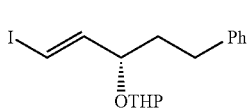
(1)

to a cuprate reagent and performing a 1,4 addition reaction between the cuprate reagent and a compound of formula (2):

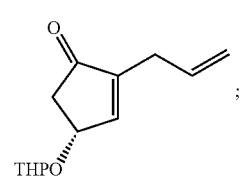
(2)

b) selectively reducing the compound of formula (3) to provide a compound of formula (4):

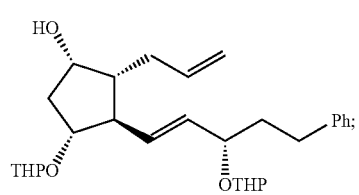
(4)

c) protecting the compound of formula (4) to provide a compound of formula (5):

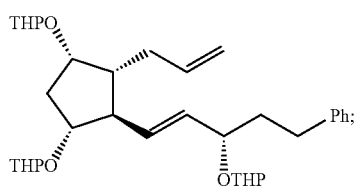

(5)

d) dihydroxylating the compound of formula (5) to provide a compound of formula (8):

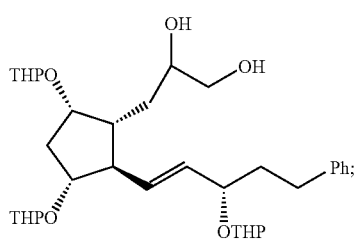

(8)

e) performing a diol cleavage reaction on the compound of formula (8) to provide a compound of formula (24):

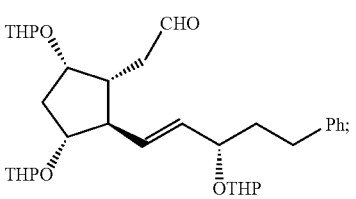

(24)

f) performing a Wittig reaction on the compound of formula (24) to provide a compound of formula (27):

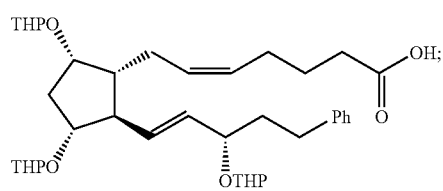

(27)

g) amidating the compound of formula (27) to provide a compound of formula (30):

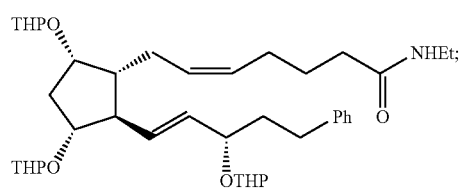

(30)

h) deprotecting the compound of formula (30) to provide Bimatoprost.

In another aspect, the invention is a process for synthesising Bimatoprost comprising the steps of:

a) preparing a compound of formula (3):

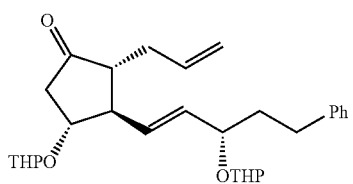

(3)

said preparing comprising converting a compound of formula (1):

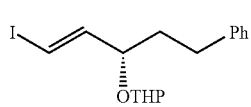

(1)

to a cuprate reagent and performing a 1,4 addition reaction between the cuprate reagent and a compound of formula (2):

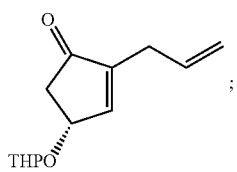

(2)

b) selectively reducing the compound of formula (3) to provide a compound of formula (4):

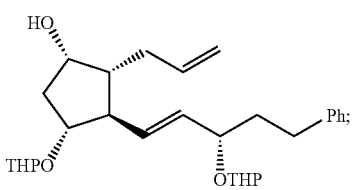

(4)

c) deprotecting the compound of formula (4) to provide a compound of formula (6):

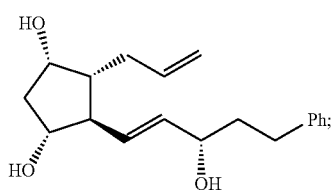

(6)

d) dihydroxylating the compound of formula (6) to provide a compound of formula (9):

(9)

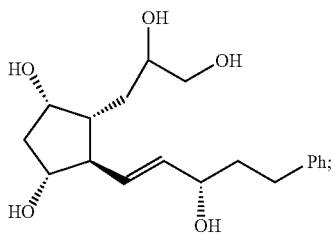

e) performing a diol cleavage on the compound of formula (9) to provide a compound of formula (25):

(25)

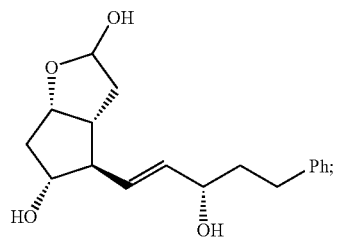

f) performing a Wittig reaction on the compound of formula (25) to provide a compound of formula (28):

(28)

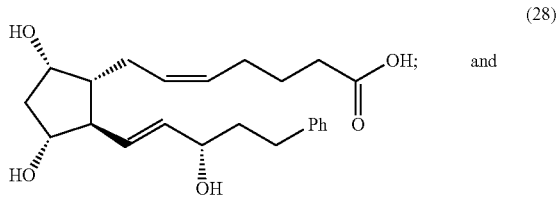 and g) amidating the compound of formula (28) to provide Bimatoprost.

In another aspect, the invention is a process for synthesising a compound of formula (IX):

(IX)

comprising the steps of:

a) reacting an acid chloride of formula (XV) with a bis(trialkylsilylacetylene) to form an acetylene of formula (XIV):

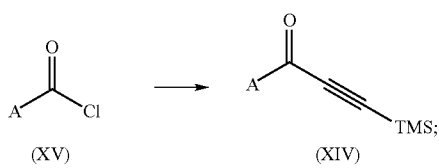

b) reacting the acetylene of formula (XIV) with a reducing agent to form an acetylene of formula (XIII):

(XIII)

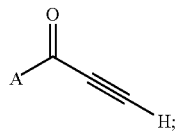

c) hydrohalogenating the acetylene of formula (XIII) to form a vinyl halide comprising a prochiral ketone according to formula (XII);

(XII)

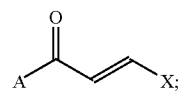

d) stereoselectively reducing the prochiral ketone in the vinyl halide of formula (XII) to form a vinyl halide comprising a hydroxy group according to formula (XI); and (XI)

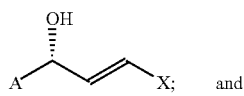 and e) protecting the hydroxy group in the vinyl halide of formula (XI) to provide the compound of formula (IX);

wherein X is a halogen; P is a hydroxyl protecting group; and A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$.

DETAILED DESCRIPTION OF THE INVENTION

The present inventors have sought to provide an alternative method of synthesising $PGF_\alpha$ prostaglandins and prostaglandin analogues. Ideally the synthetic route will be generally applicable to a variety of prostaglandin compounds and will provide high yields. Accordingly, the present invention provides a process for the preparation of prostaglandin compounds having the formula (I):

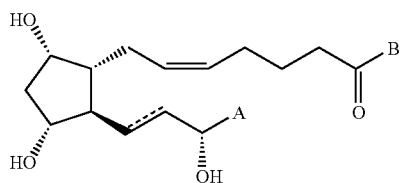

(I)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_nOR'$ wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; B is selected from OR" and NHR" wherein R" is $C_1$–$C_6$ alkyl; and

- - - - - represents a double bond or a single bond.

Scheme 1 shows the synthesis of prostaglandins of formula (I) starting from an allyl cyclopentenone (X) and a substituted alkene (IX) (P is a hydroxyl protecting group):

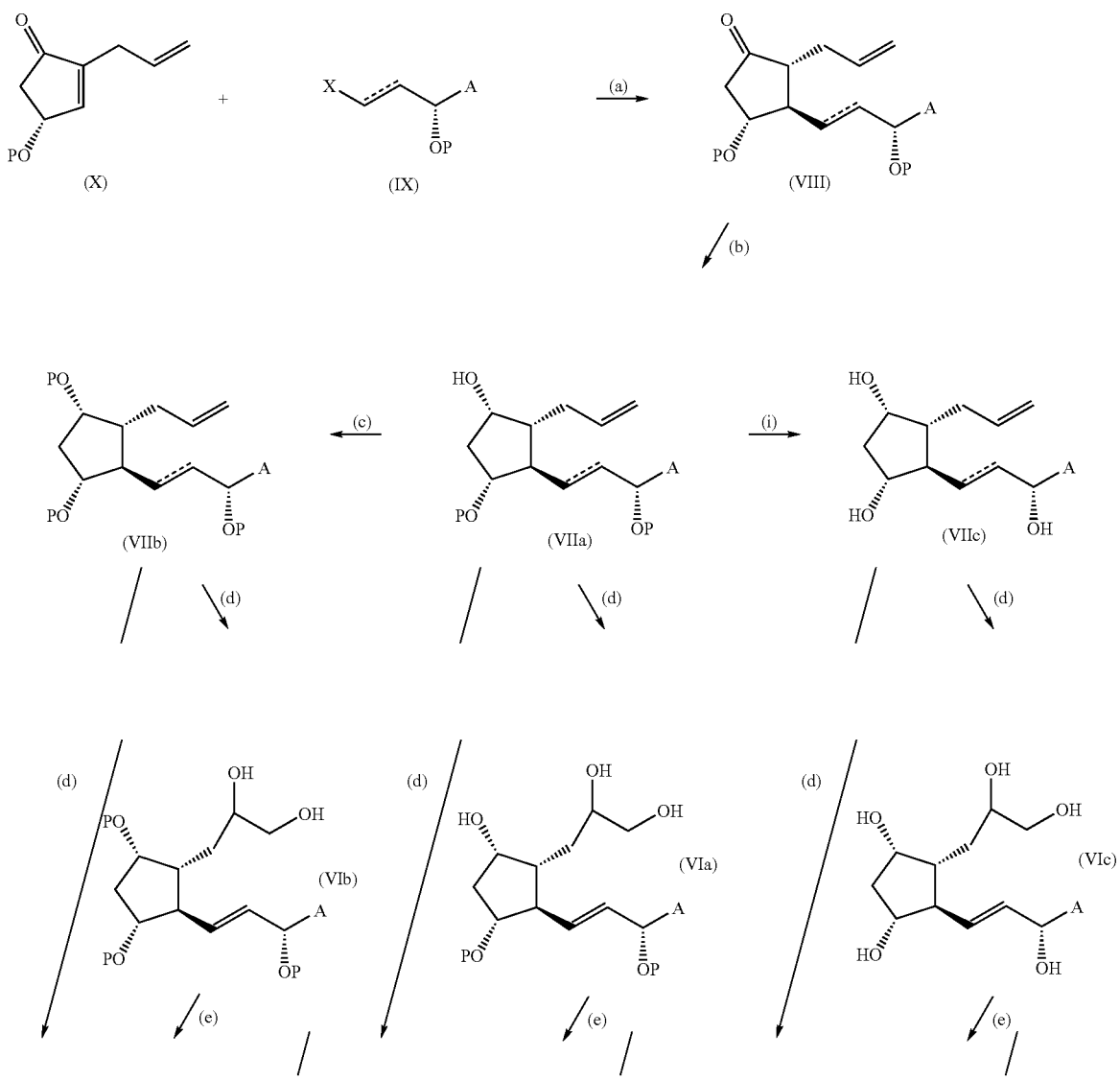

Scheme 1

-continued
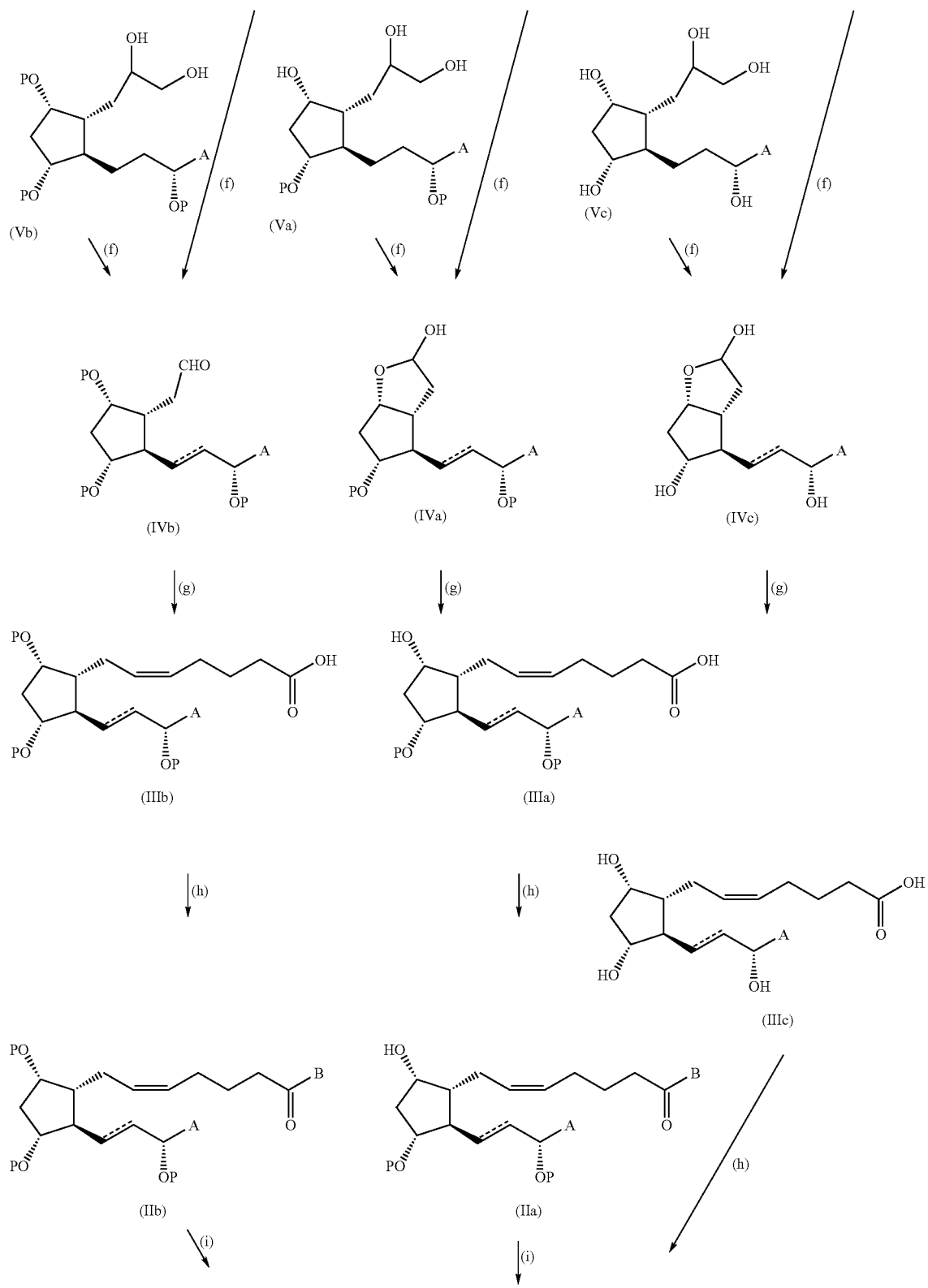

-continued

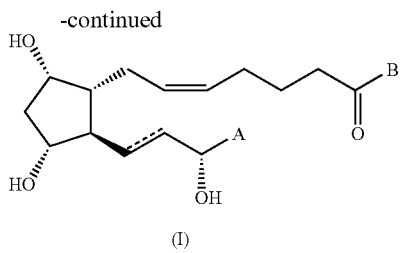

(I)

(a) 1,4 addition of a cuprate reagent formed from compound of formula (IX); (b) stereoselective reduction; (c) protection with a hydroxyl protecting group; (d) dihydroxylation; (e) reduction; (f) diol cleavage; (g) Wittig reaction: (h) esterification or amidation; (i) deprotection.

In one aspect the present invention provides a process for the preparation of a compound of Formula (VIII):

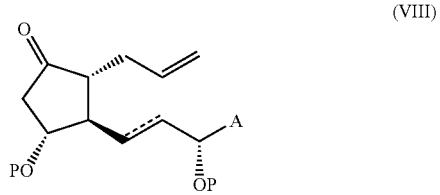

(VIII)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; P is a hydroxyl protecting group and

----- represents a double bond or a single bond; wherein a compound of Formula (IX):

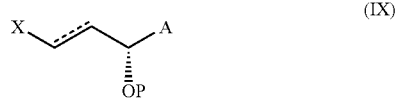

(IX)

wherein A, P and

----- are as defined above and X is a leaving group, is reacted to form a cuprate reagent which undergoes a 1,4 addition reaction with a compound of Formula (X):

(X)

wherein P is as defined above.

Suitably, P is a tetrahydropyranyl (THP) or silyl ether protecting group. Preferably P is a THP protecting group. Suitably X is a halogen, preferably iodine.

Techniques for forming suitable cuprate reagents from compounds of Formula (IX) are well known to the person skilled in the art. For example, compounds wherein X is iodine can be reacted with a lithiated alkane, e.g. n-BuLi, in a solvent such as tetrahydrofuran (THF) or tert-butyl methyl ether (TBME) at −78° C. for one hour. Subsequently, copper cyanide and methyl lithium are added to the reaction mixture, and the temperature rises to 0° C. over 45 minutes. The cuprate reagent is formed in the reaction mixture. The cyclopentenone of formula (X) can be added to the reaction mixture, preferably at −78° C., and the cuprate reagent will undergo 1,4 addition to compound (X), forming compound (VIII).

Compounds of formula (IX), wherein

----- represents a double bond and X is a halogen, can be made by a process comprising the following steps:
a) reaction of an acid chloride of formula (XV) with a bis(trialkylsilylacetylene) to form an acetylene of formula (XIV);
b) reaction of the acetylene of formula (XIV) with a reducing agent to form an acetylene of formula (XIII);
c) hydrohalogenation of the acetylene of formula (XIII) to form a vinyl halide of formula (XII);
d) stereoselective reduction of the prochiral ketone in the vinyl halide of formula (XII) to form a vinyl halide of formula (XI); and
e) protection of the hydroxy group in the vinyl halide of formula (XI).

Preferred reactants are shown in the following reaction scheme:

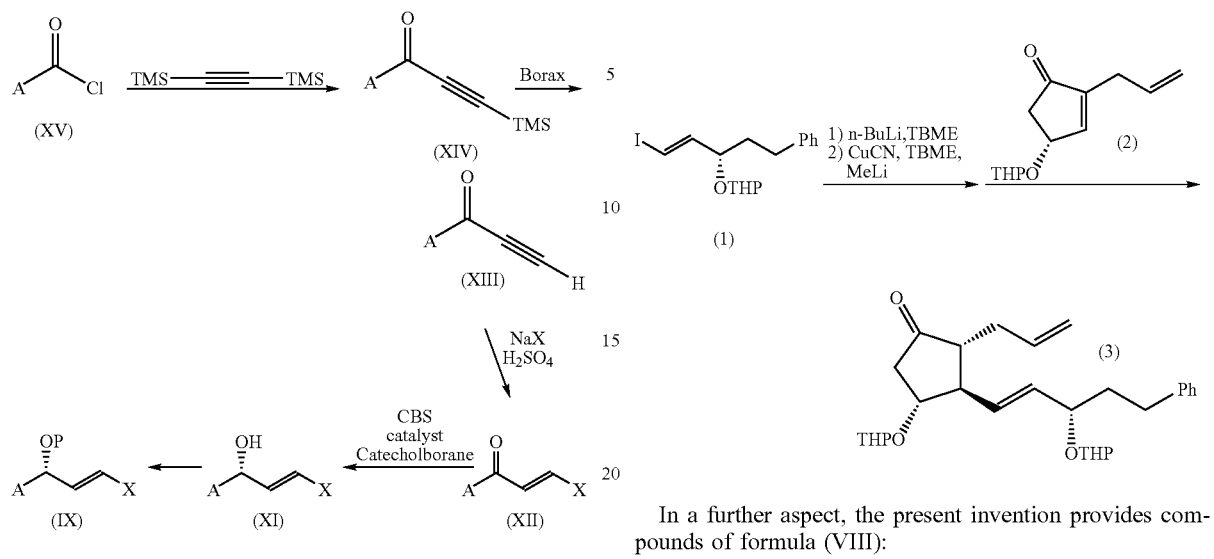

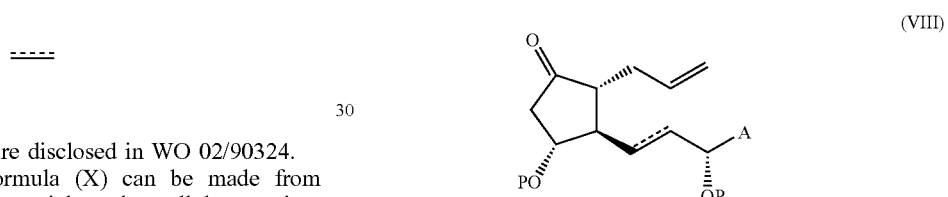

Methods of synthesising compounds of formula (IX) wherein

----- represents a single bond are disclosed in WO 02/90324.

Cyclopentenones of formula (X) can be made from readily available starting materials such as allylmagnesium chloride and 2-furaldehyde:

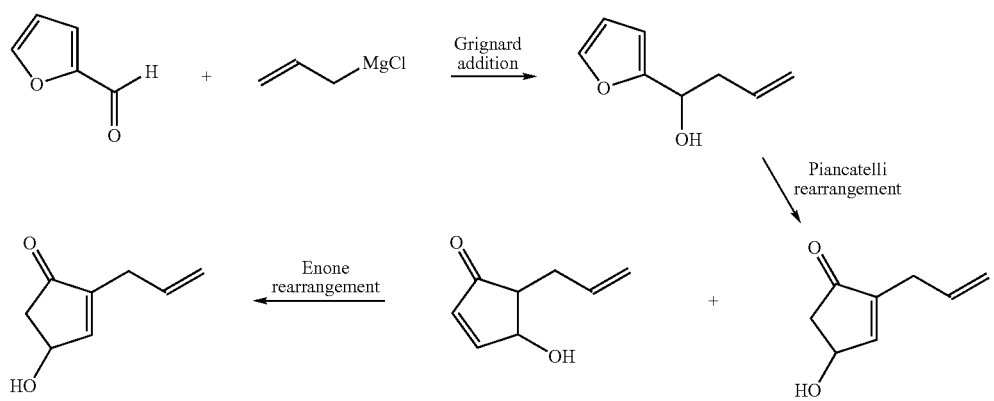

The racemic cyclopentenone can be resolved using standard techniques and the alcohol should be protected. Other methods of forming cyclopentenones of formula (X) are disclosed in EP 115 680.

In a preferred embodiment of the invention, A is $(CH_2)_2Ph$,

----- represents a double bond, P is THP and X is I:

In a further aspect, the present invention provides compounds of formula (VIII):

(VIII)

wherein A, P and

----- are as defined above.

In a preferred embodiment the present invention provides a compound of formula (VIII) wherein A is $(CH_2)_2Ph$, represents a double bond and P is THP:

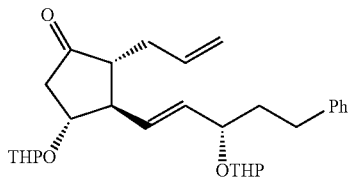
(3)

In a further aspect the invention provides a process for the preparation of a compound of formula (VIIa):

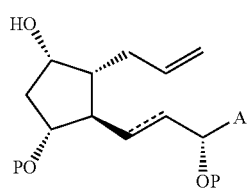
(VIIa)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$ OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; P is a hydroxyl protecting group and

- - - - - represents a double bond or a single bond; wherein a compound of Formula (VIII):

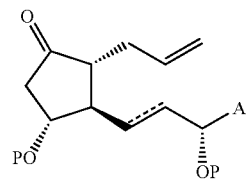
(VIII)

wherein A, P and

- - - - - are as defined above, undergoes selective reduction.

Suitably, P is a tetrahydropyranyl (THP) or silyl ether protecting group. Preferably P is a THP protecting group.

Suitable selective reduction reagents are well known to the skilled person. Preferably the ketone is selectively reduced using L-Selectride in tetrahydrofuran (THF) solvent at −78° C.

In a preferred embodiment, A is $(CH_2)_2Ph$,

- - - - - represents a double bond and P is THP:

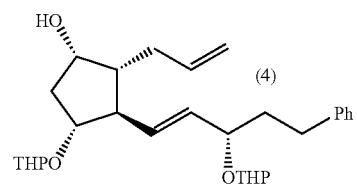

In a further aspect, the present invention provides compounds of formula (VIIa):

(VIIa)

wherein A, P and

- - - - - are as defined above.

In a preferred embodiment the present invention provides a compound of formula (VIIa) wherein A is $(CH_2)_2Ph$, represents a double bond and P is THP:

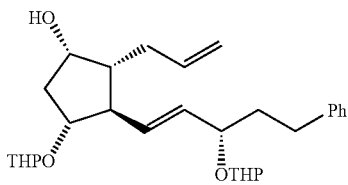

(4)

In a further aspect the invention provides a process for the preparation of a compound of formula (VIIb):

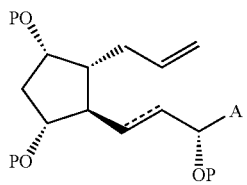

(VIIb)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; P is a hydroxyl protecting group and

----- represents a double bond or a single bond; wherein a compound of Formula (VIIa):

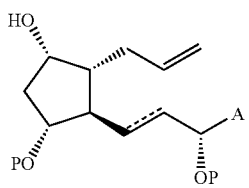

(VIIa)

wherein A, P and

----- are as defined above, is protected with a hydroxyl protecting group.

Suitably, P is a tetrahydropyranyl (THP) or silyl ether protecting group. Preferably P is a THP protecting group.

Methods of protecting hydroxyl groups are well known to the skilled person. If P is THP, the hydroxyl group can be protected by reaction with 2,3-dihydro-4H-pyran (DHP) and pyridinium p-toluenesulfonate (PPTS) at room temperature in a dichloromethane (DCM) solvent.

In a preferred embodiment, A is $(CH_2)_2Ph$,

----- represents a double bond and P is THP:

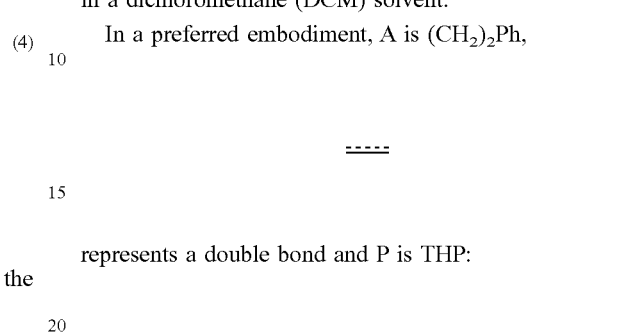

In a further aspect, the present invention provides compounds of formula (VIIb):

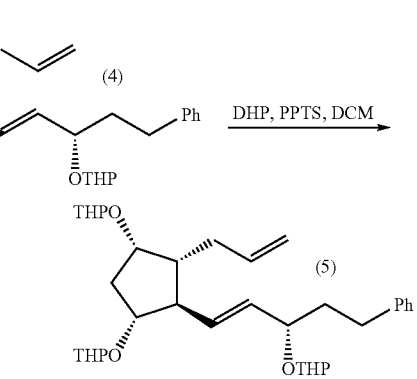

(VIIb)

wherein A, P and

----- are as defined above.

In a preferred embodiment the present invention provides a compound of formula (VIIb) wherein A is $(CH_2)_2Ph$,

----- represents a double bond and P is THP:

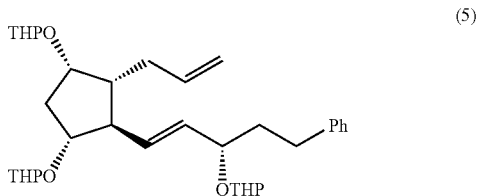

(5)

In a further aspect the invention provides a process for the preparation of a compound of formula (VIc):

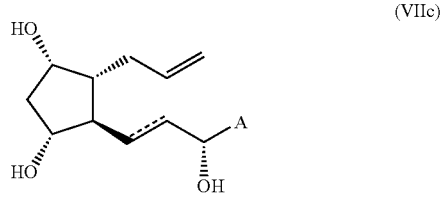

(VIIc)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$OR' wherein n is an integer from 1 to 3 and R' represents a $C_6$–$C_0$ aryl group which is optionally substituted with one to three substituents selected from the group consisting of $C_1$–$C_6$ alkyl, halo and $CF_3$ and

----- represents a double bond or a single bond;

wherein a compound of Formula (VIIa):

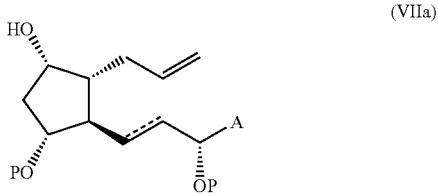

(VIIa)

wherein A, P and

----- are as defined above, is deprotected.

Suitably, P is a tetrahydropyranyl (THP) or silyl ether protecting group. Preferably P is a THP protecting group.

Methods of deprotecting protected hydroxyl groups are well known to the skilled person. If P is THP, the hydroxyl groups can be removed by reaction by reaction with pyridinium p-toluenesulfonate (PPTS) in a methanol solvent.

In a preferred embodiment, A is $(CH_2)_2Ph$ and

----- represents a double bond:

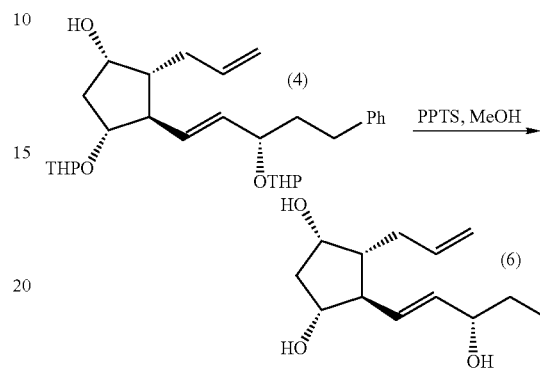

In a further aspect, the present invention provides compounds of formula (VIIc):

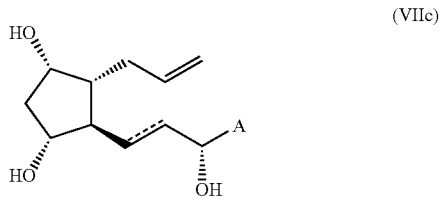

(VIIc)

wherein A and

----- are as defined above.

In a preferred embodiment the present invention provides a compound of formula (VIIc) wherein A is $(CH_2)_2Ph$ and

----- represents a double bond:

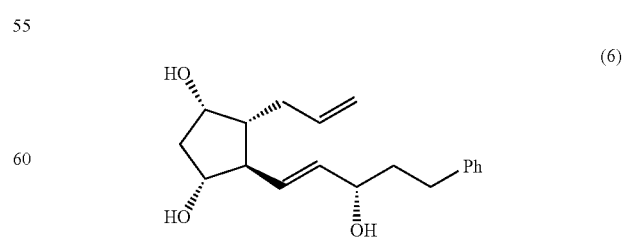

(6)

In a further aspect the invention provides a process for the preparation of a compound of formula (VIa), (VIb), (VIc), (Va), (Vb) or (Vc):

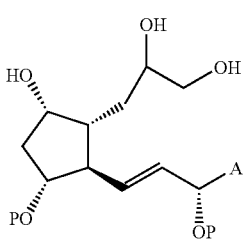
(VIa)

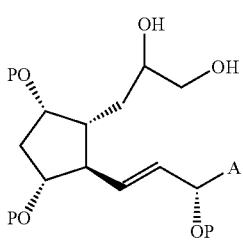
(VIb)

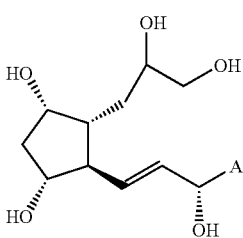
(VIc)

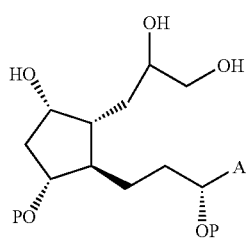
(Va)

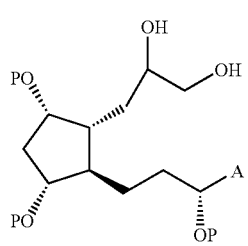
(Vb)

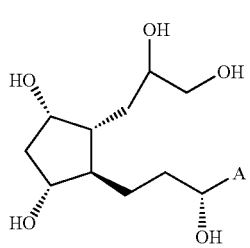
(Vc)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$ OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; and P is a hydroxyl protecting group;

wherein a compound of Formula (VIIa), a compound of Formula (VIIb) or a compound of Formula (VIIc):

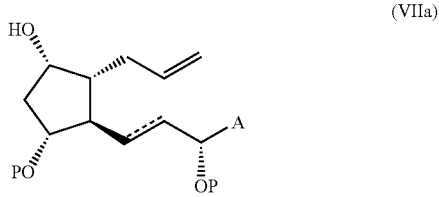
(VIIa)

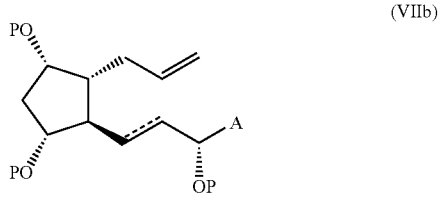
(VIIb)

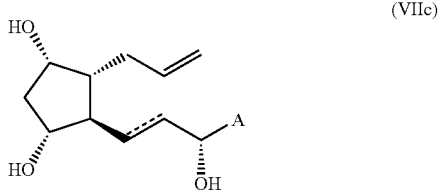
(VIIc)

wherein A and P are as defined above and

----- is a double or single bond, undergoes dihydroxylation.

If there is more than one double bond in the compound of formula (VIIa), (VIIb) or (VIIc), then it is the terminal double bond that undergoes dihydroxylation.

Suitably, P is a tetrahydropyranyl (THP) or silyl ether protecting group. Preferably P is a THP protecting group.

Suitable methods of dihydroxylating double bonds are well known to the skilled person. A preferred reagent is N-methyl morpholine-N-oxide (NMO) in the presence of catalytic amounts of osmium tetroxide. The solvent is preferably a 4:1 mixture of tetrahydrofuran (THF) and water. The reaction is suitably carried out from −10 to −4° C.

In a preferred embodiment, A is $(CH_2)_2Ph$, P is THP,

----- represents a double bond, and (VIIa) is reacted to give (VIa):

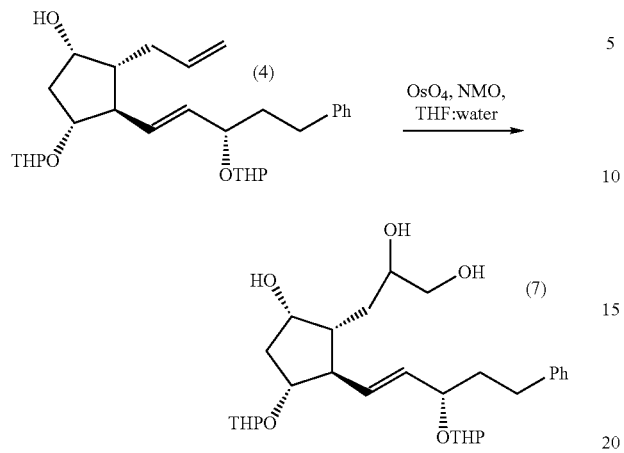
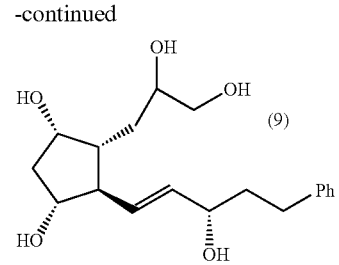
In a second preferred embodiment, A is $(CH_2)_2Ph$, P is THP,
-----
represents a double bond, and (VIIb) is reacted to give (VIb):
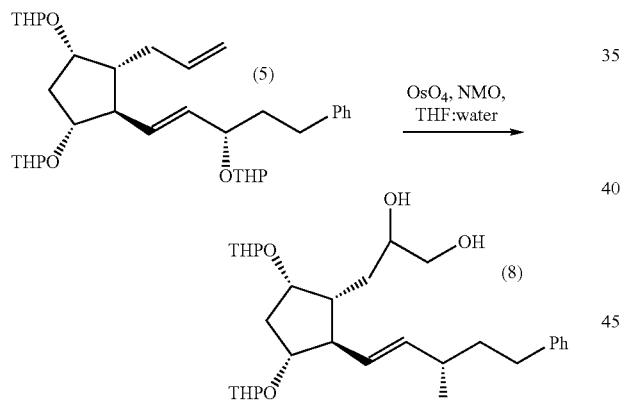
In a third preferred embodiment, A is $(CH_2)_2Ph$,
-----
represents a double bond, and (VIIc) is reacted to give (VIc):
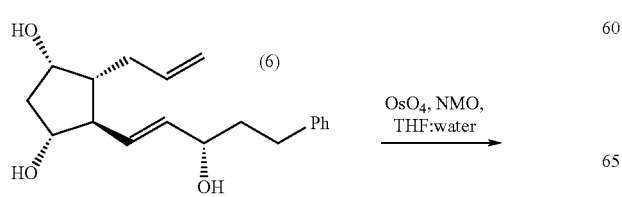
In a further aspect, the present invention provides compounds of formula (VIa), (VIb) (VIc), (Va), (Vb) and (Vc):
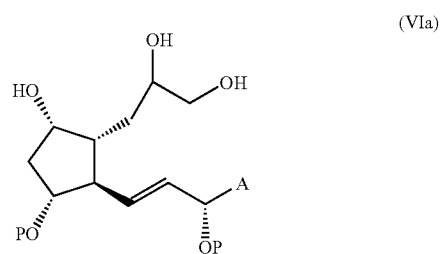
(VIa)
(VIb)
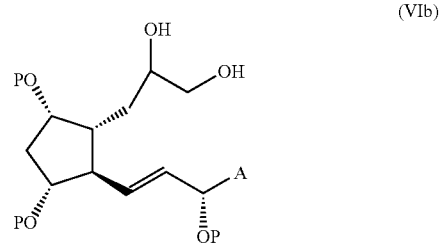
(VIc)
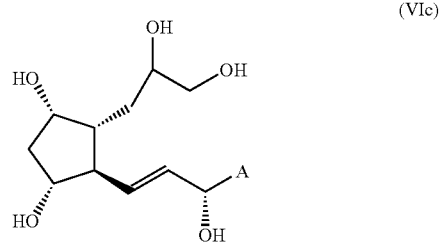
(Va)
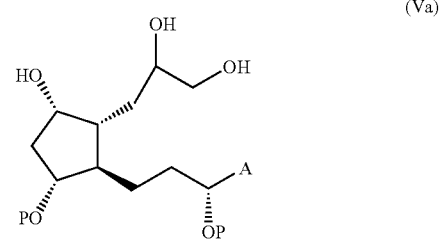
(Vb)
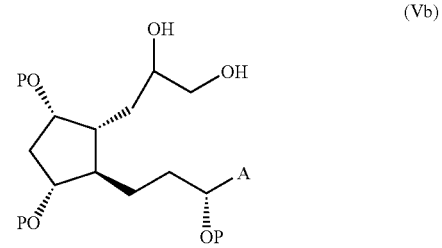

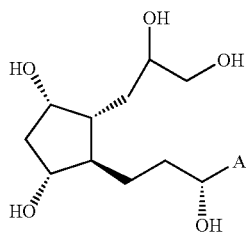
(Vc)

wherein A and P are as defined above.

In a preferred embodiment the present invention provides compounds of formula (VIa), (VIb), (Va) and (Vb) wherein A is $(CH_2)_2Ph$ and P is THP, and compounds of formula (VIc) and (Vc) wherein A is $(CH_2)_2Ph$:

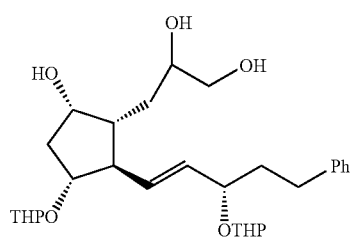
(7)

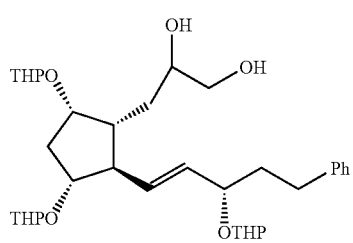
(8)

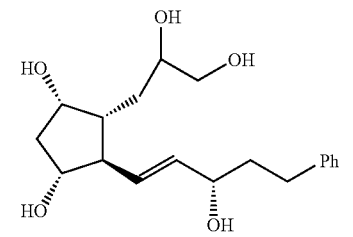
(9)

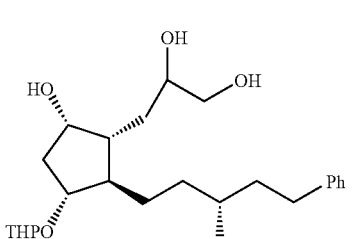
(10)

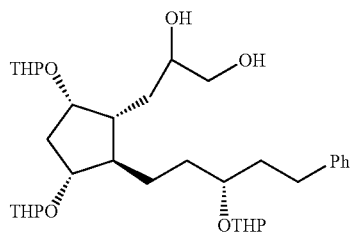
(11)

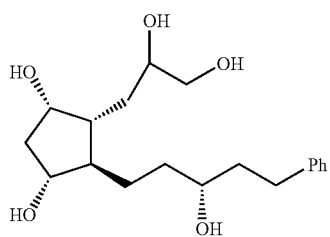
(12)

In a further aspect the invention provides a process for the preparation of a compound of formula (Va), (Vb) or (Vc):

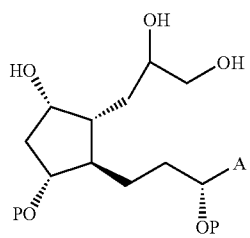
(Va)

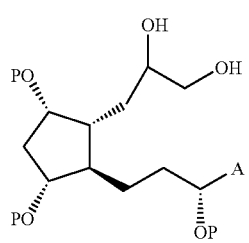
(Vb)

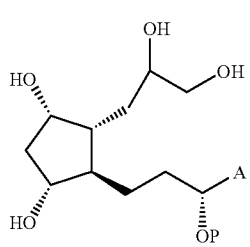
(Vc)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$ OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; and P is a hydroxyl protecting group;

wherein a compound of Formula (VIa), a compound of Formula (VIb) or a compound of Formula (VIc):

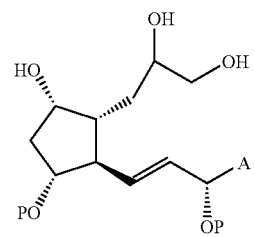
(VIa)

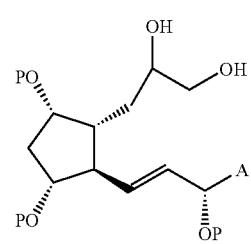
(VIb)

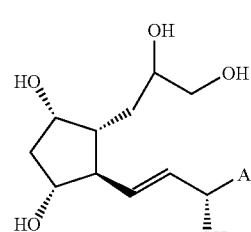
(VIc)

wherein A and P are as defined above, undergoes reduction of the double bond.

Suitably, P is a tetrahydropyranyl (THP) or silyl ether protecting group. Preferably P is a THP protecting group.

Suitable methods of reducing double bonds are well known to the skilled person. In a preferred method, the double bond is hydrogenated, e.g. by passing hydrogen gas at a pressure of 40 psi into the reaction mixture which comprises a 5% Pd on carbon catalyst in an ethanol solvent.

In a preferred embodiment, A is $(CH_2)_2Ph$, P is THP and (VIa) is reacted to give (Va):

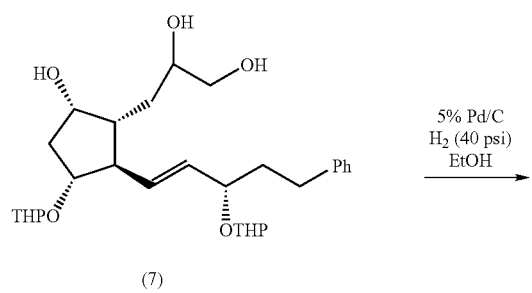
(7)

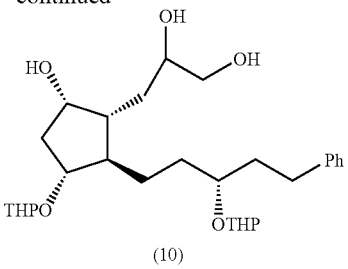
(10)

In a second preferred embodiment, A is $(CH_2)_2Ph$, P is THP and (VIb) is reacted to give (Vb):

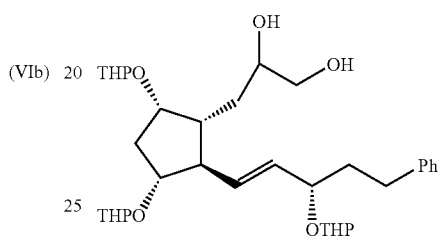
(8)

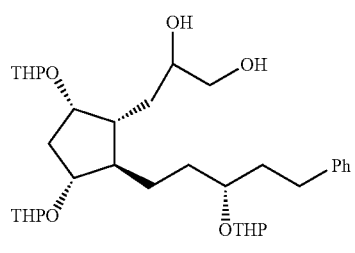
(11)

In a third preferred embodiment, A is $(CH_2)_2Ph$ and (VIc) is reacted to give (Vc):

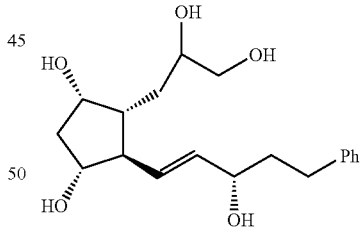
(9)

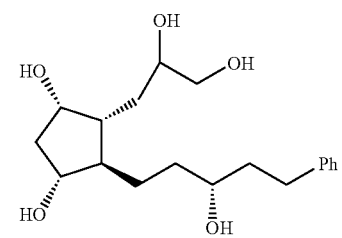
(12)

In a further aspect the invention provides a process for the preparation of a compound of formula (IVa), (IVb) or (IVc):

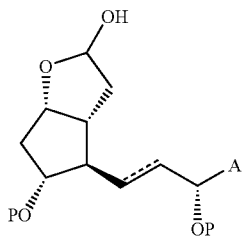
(IVa)

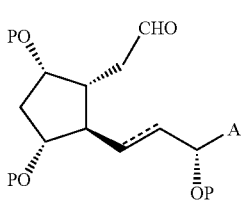
(IVb)

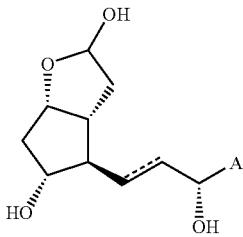
(IVc)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$ OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; P is a hydroxyl protecting group and

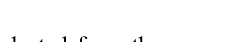

represents a double bond or a single bond; wherein a compound of Formula (VIa), (Va), (VIb), (Vb), (VIc) or (Vc):

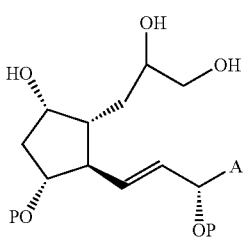
(VIa)

-continued

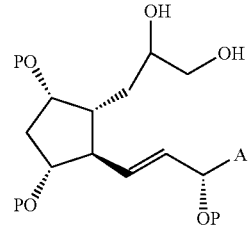
(VIb)

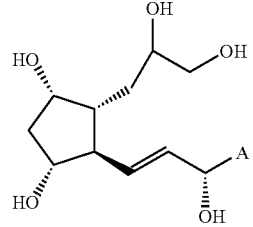
(VIc)

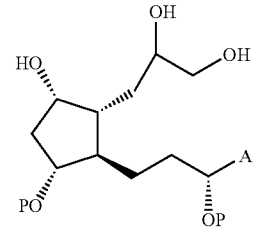
(Va)

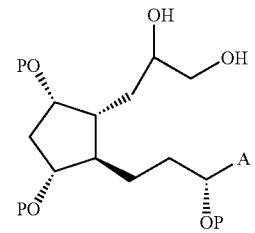
(Vb)

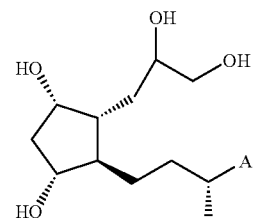
(Vc)

wherein A and P are as defined above, undergoes diol cleavage.

Suitably, P is a tetrahydropyranyl (THP) or silyl ether protecting group. Preferably P is a THP protecting group.

Suitable methods of diol cleavage are well known to the skilled person. A preferred method uses two equivalents of sodium periodate and silica in a 1:1 ratio. A suitable solvent is a mixture of water and dichloromethane.

In a preferred embodiment, A is $(CH_2)_2Ph$, P is THP,

- - - - - represents a single bond, and (Va) is reacted to give (IVa):

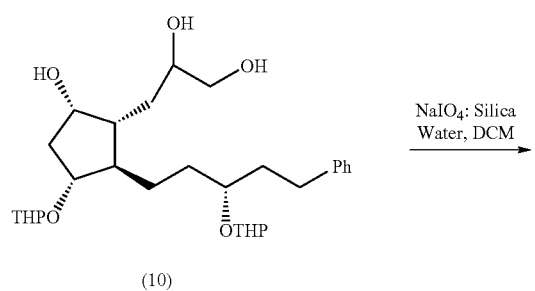

(10)

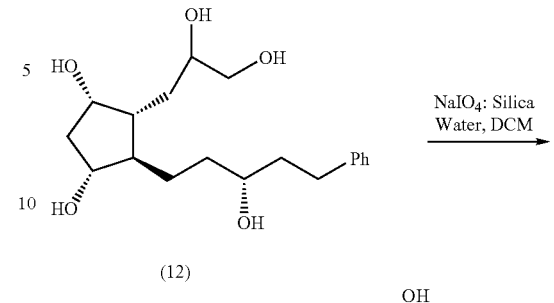

(12)

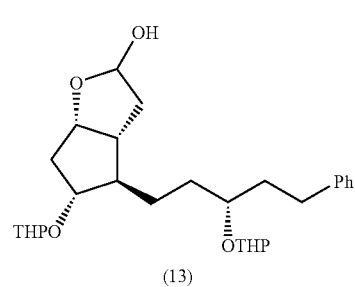

(13)

In a second preferred embodiment, A is (CH$_2$)$_2$Ph, P is THP,

----- represents a single bond, and (Vb) is reacted to give (IVb):

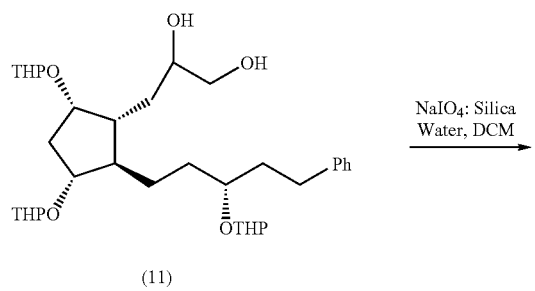

(11)

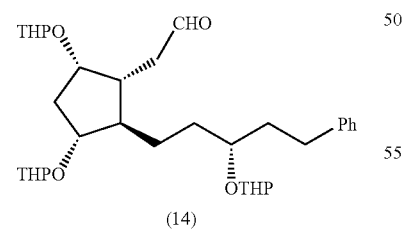

(14)

In a third preferred embodiment, A is (CH$_2$)$_2$Ph,

----- represents a single bond, and (Vc) is reacted to give (IVc):

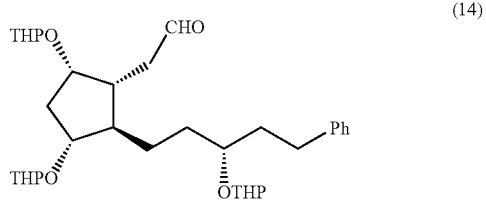

(15)

In a further aspect, the present invention provides a compound of formula (IVb) wherein A is (CH$_2$)$_2$Ph, P is THP and

----- is a single bond:

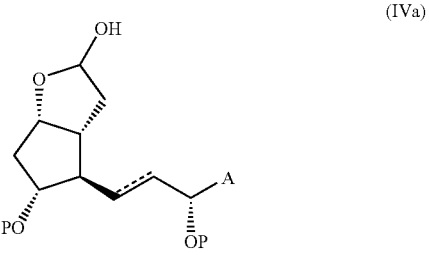

(14)

Compounds of formula (IVa), (IVb) or (IVc):

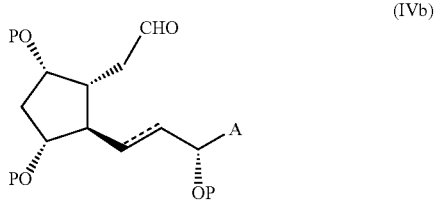

(IVa)

(IVb)

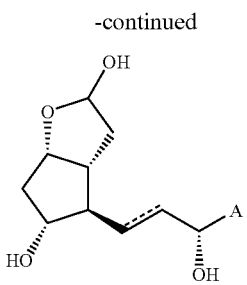

(IVc)

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; P is a hydroxyl protecting group and

----- represents a double bond or a single bond; can be reacted with Wittig reagents to give compounds of formula (IIIa), (IIIb) and (IIIc):

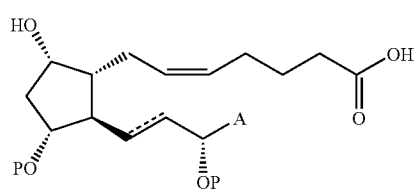

(IIIa)

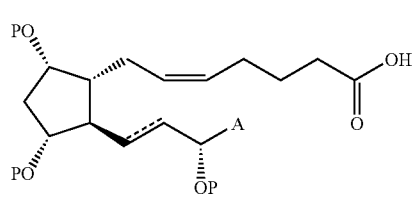

(IIIb)

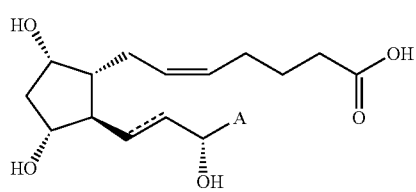

(IIIc)

wherein A, P and

----- are as defined above.

Suitable Wittig reagents will be well known to the person skilled in the art. A preferred Wittig reagent is (4-Carboxybutyl)triphenylphosphonium bromide and this is reacted with the compound of formula (IVa), (IVb) or (IVc) and potassium t-butoxide in tetrahydrofuran (THF) solvent at 0° C.

For example, a compound of formula (IVa) wherein A is $(CH_2)_2Ph$, P is THP,

----- represents a single bond is reacted to give a compound of formula (IIIa):

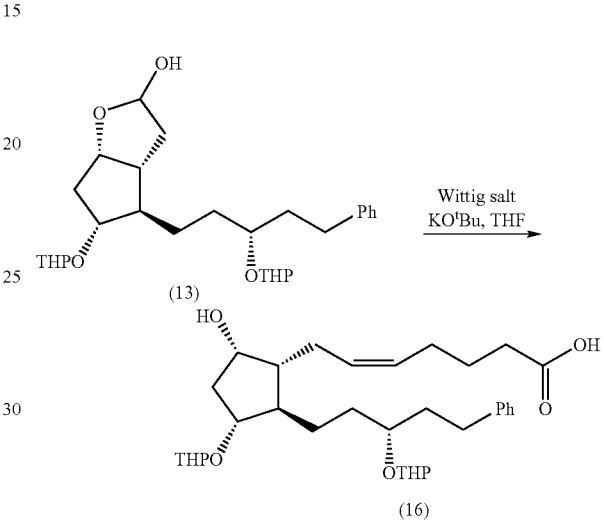

In a second example, a compound of formula (IVb) wherein A is $(CH_2)_2Ph$, P is THP,

----- represents a single bond is reacted to give a compound of formula (IIIb):

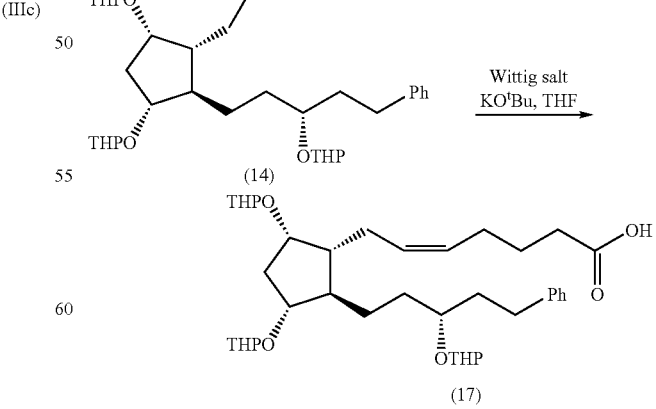

In a third example, a compound of formula (IVc) wherein A is $(CH_2)_2Ph$ and represents a single bond is reacted to give a compound of formula (IIIc):

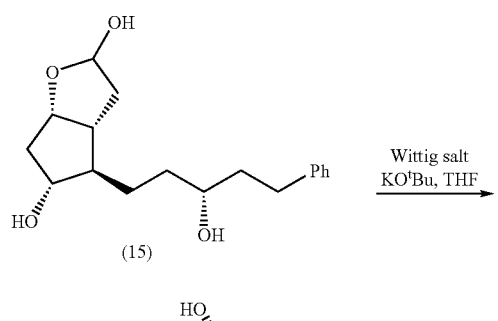

Compounds of formula (IIIa), (IIb) or (IIIc):

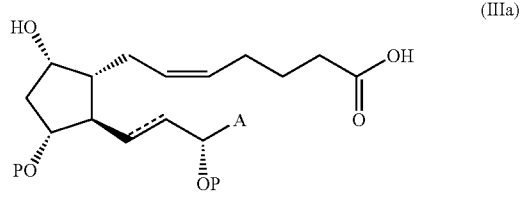

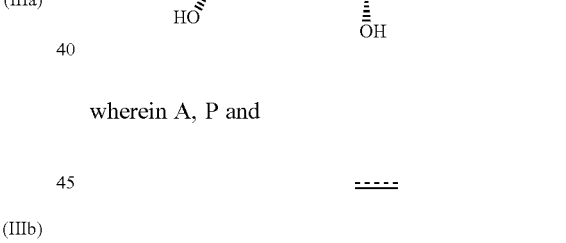

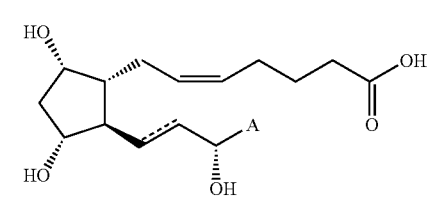

wherein A is selected from the group consisting of $C_1$–$C_6$ alkyl; $C_7$–$C_{16}$ aralkyl wherein the aryl group is optionally substituted with one to three substituents selected from the group consisting of $C_1$–$C_6$ alkyl, halo and $CF_3$; and $(CH_2)_n$OR' wherein n is an integer from 1 to 3 and R' represents a $C_6$–$C_{10}$ aryl group which is optionally substituted with one to three substituents selected from the group consisting of $C_1$–$C_6$ alkyl, halo and $CF_3$; P is a hydroxyl protecting group and represents a double bond or a single bond; can be esterified or amidated to give compounds of formula (IIa), (IIb) and (I):

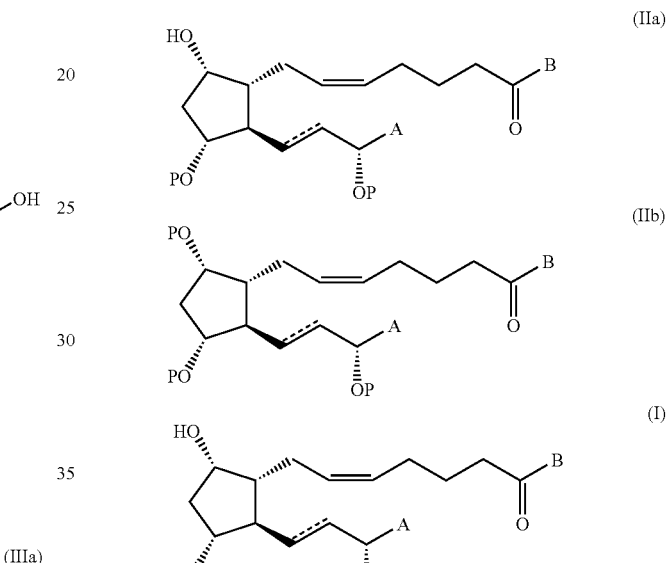

wherein A, P and are as defined above, and B is selected from OR" and NHR" wherein R" is $C_1$–$C_6$ alkyl.

Suitable esterification/amidation reagents will be well known to the person skilled in the art. A preferred esterification reagent is 2-iodopropane (isopropyl iodide) and the reaction mixture further comprises a base such as 1,8-diazabicyclo[5.4.0]undec-7-ene (DBU). Acetone is a suitable solvent. A preferred amidation reagent is ethylamine (EtNH$_2$) and the reaction mixture suitably further comprises 1-(3-Dimethylaminopropyl)-3-ethylcarbodiimide hydrochloride (EDC-HCl).

For example, a compound of formula (IIIa) wherein A is $(CH_2)_2Ph$, P is THP and represents a single bond, is esterified to give a compound of formula (IIa):

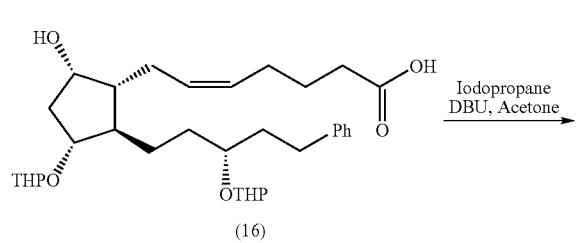

(16)

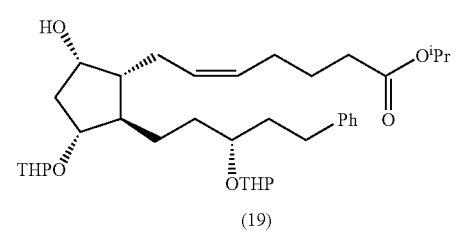

(19)

In a second example, a compound of formula (IIIa) wherein A is (CH$_2$)$_2$Ph, P is THP and

----- represents a double bond is amidated, to give a compound of formula (IIa):

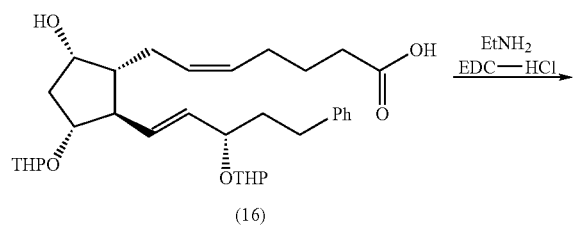

(16)

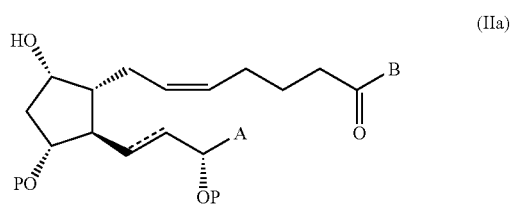

(20)

In a third example, a compound of formula (IIIc) wherein A is (CH$_2$)$_2$Ph and

----- represents a single bond, is esterified to give a compound of formula (I) which is commonly known as Latanoprost:

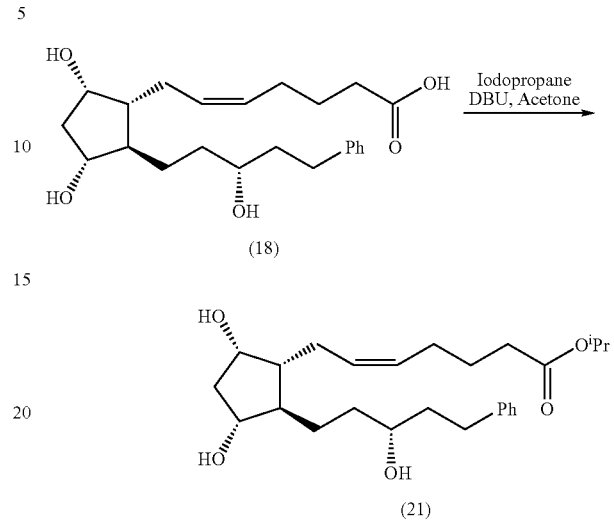

(18)

(21)

Compounds of formula (IIa) or (IIb):

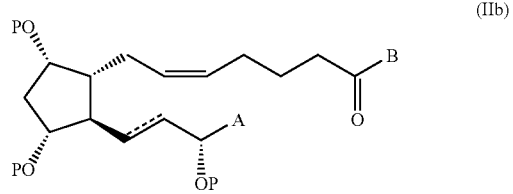

wherein A is selected from the group consisting of C$_1$–C$_6$ alkyl; C$_7$–C$_{16}$ aralkyl wherein the aryl group is optionally substituted with one to three substituents selected from the group consisting of C$_1$–C$_6$ alkyl, halo and CF$_3$; and (CH$_2$)$_n$OR' wherein n is an integer from 1 to 3 and R' represents a C$_6$–C$_{10}$ aryl group which is optionally substituted with one to three substituents selected from the group consisting of C$_1$–C$_6$ alkyl, halo and CF$_3$; P is a hydroxyl protecting group,

----- represents a double bond or a single bond and B is selected from OR" and NHR" wherein R" is C$_1$–C$_6$ alkyl; can be deprotected to give compounds of formula (I):

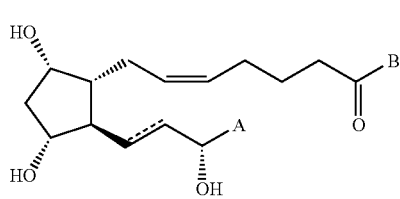

wherein A, B and

----- are as defined above.

Suitable deprotection reagents are well known to the person skilled in the art. A preferred reagent is pyridinium p-toluenesulfonate (PPTS) in a methanol solvent.

For example, a compound of formula (IIa) wherein A is $(CH_2)_2Ph$, P is THP,

----- represents a single bond and B is $O^iPr$, can be deprotected to give a compound of formula (I) which is commonly known as Latanoprost:

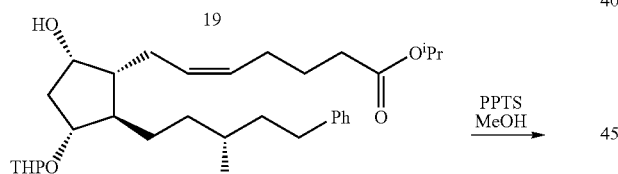

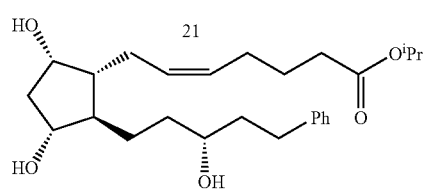

In a second example, a compound of formula (IIa) wherein A is $(CH_2)_2Ph$, P is THP,

----- represents a double bond and B is NHEt can be deprotected to give a compound of formula (I) which is commonly known as Bimatoprost:

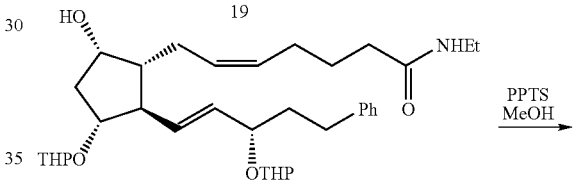

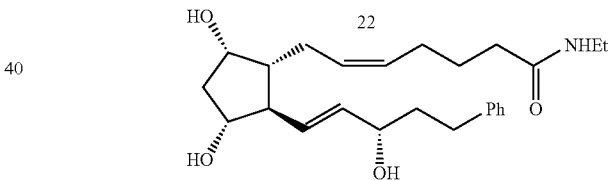

The present invention further provides methods for synthesising Latanoprost as shown in Scheme 2:

Scheme 2

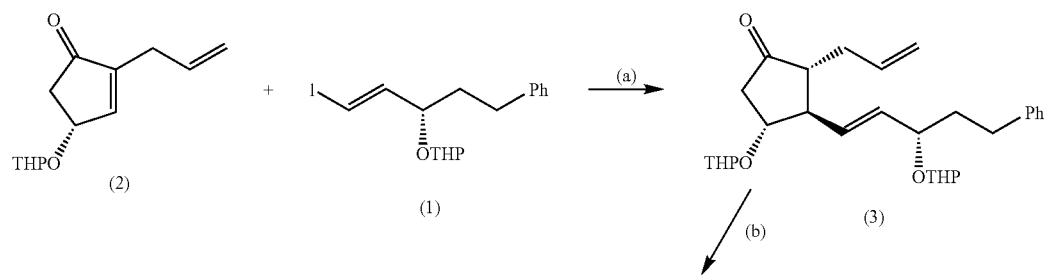

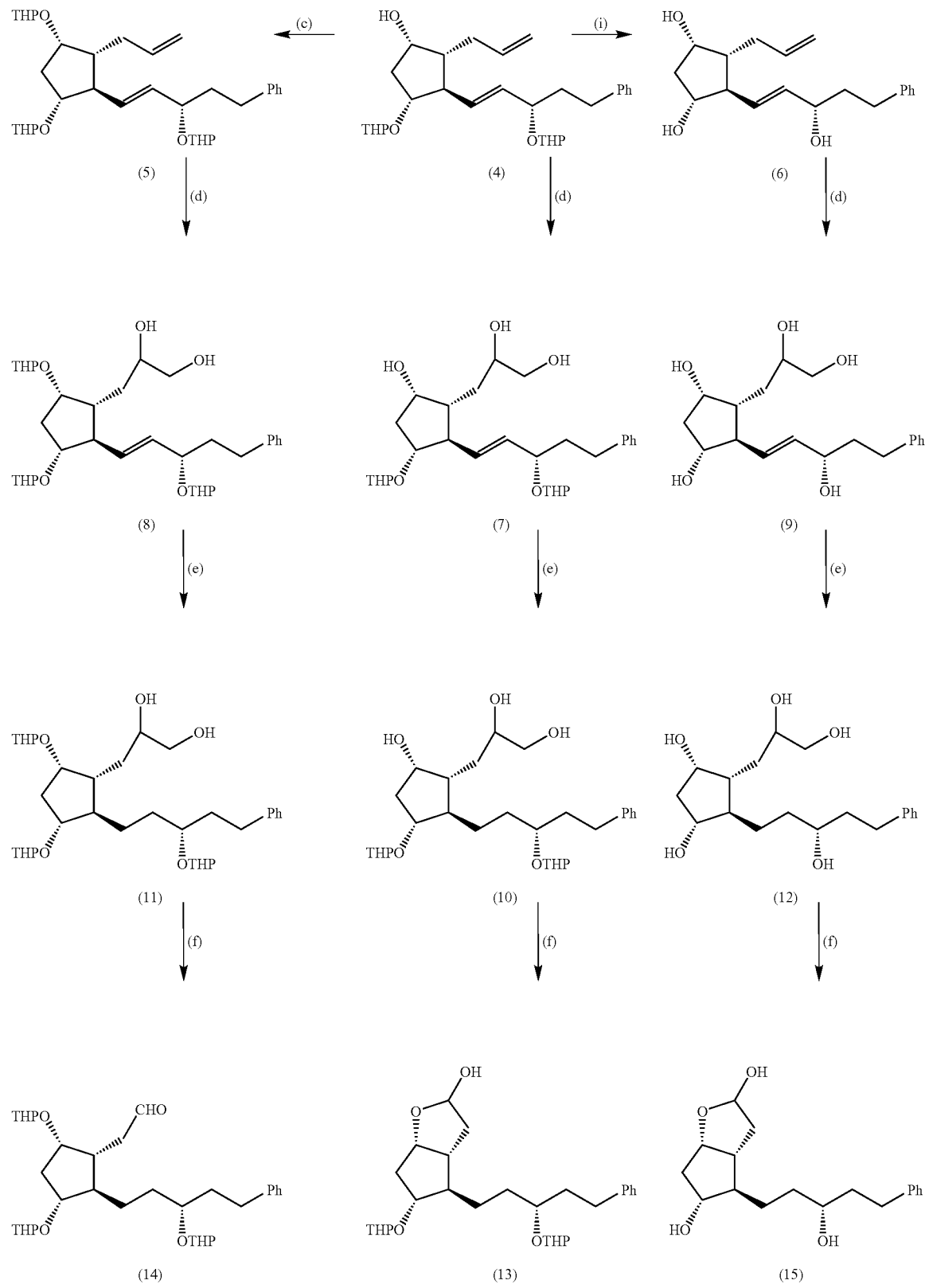

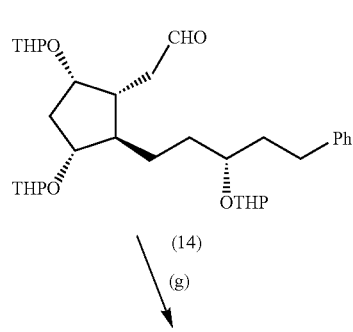
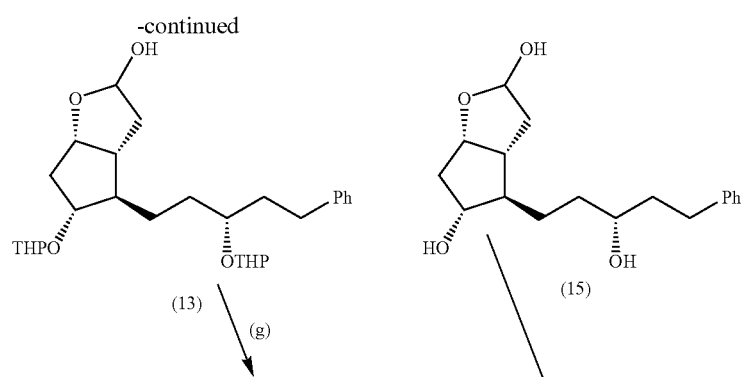
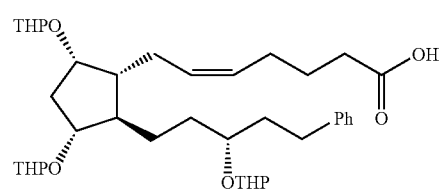
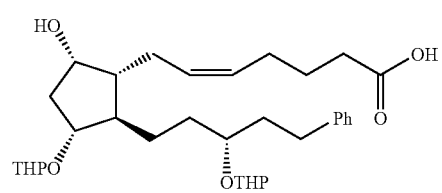
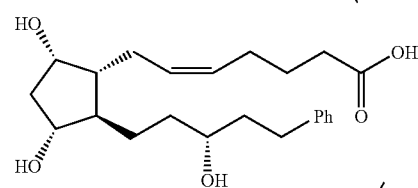
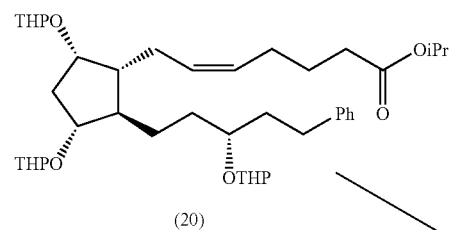
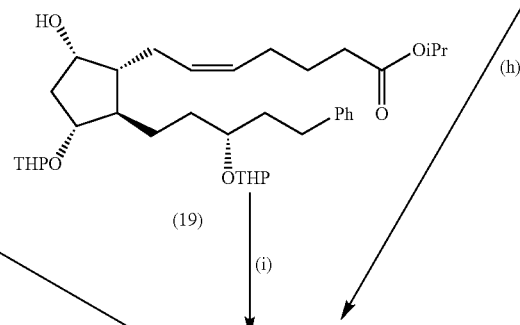
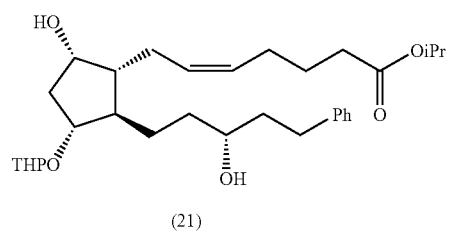

(a) 1,4 addition of a cuprate reagent formed from compound of formula (IX); (b) stereoselective reduction; (c) protection with a hydroxyl protecting group; (d) dihydroxylation; (e) reduction; (f) diol cleavage; (g) Wittig reaction; (h) esterification; (i) deprotection.
The present invention further provides methods for synthesising Bimatoprost as shown in Scheme 3:
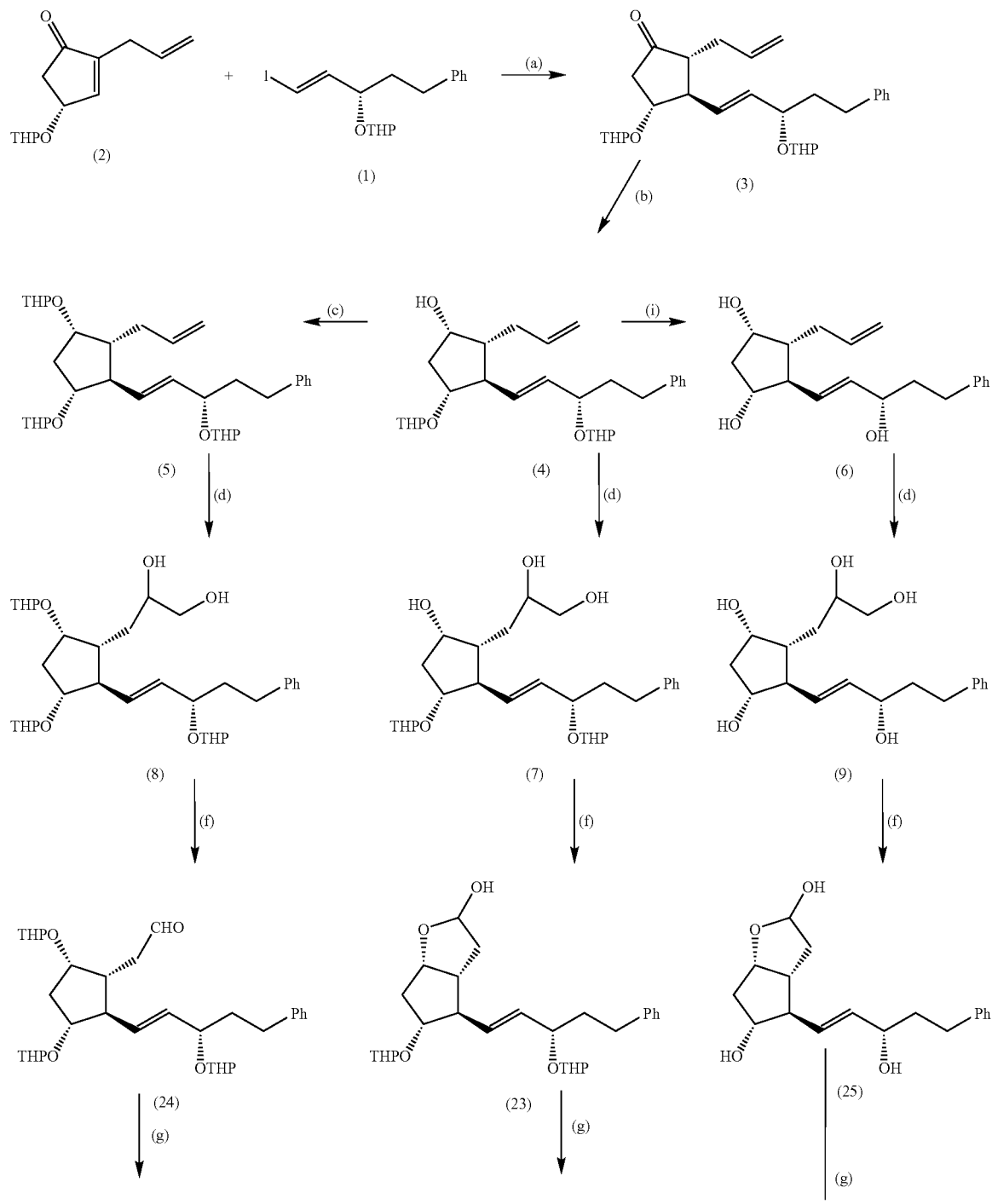
Scheme 3

-continued
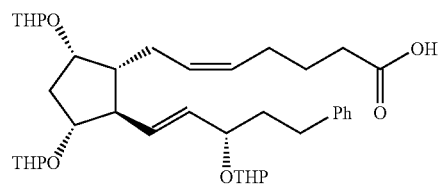
(27)
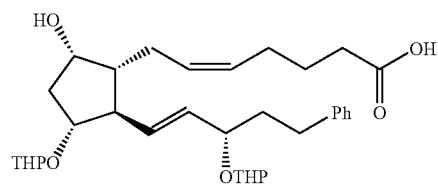
(26)
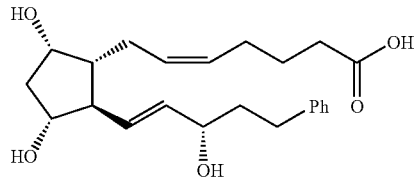
(28)
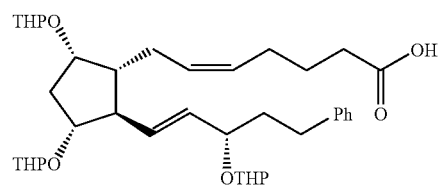
(27)
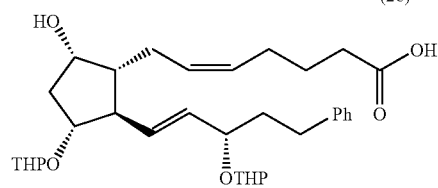
(26)
↓ (h)          ↓ (h)
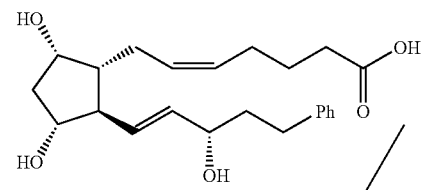
(28)
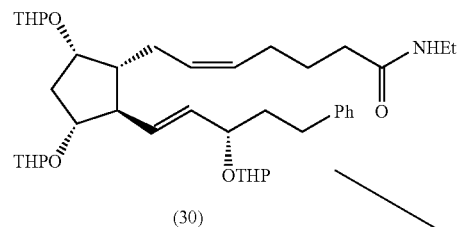
(30)
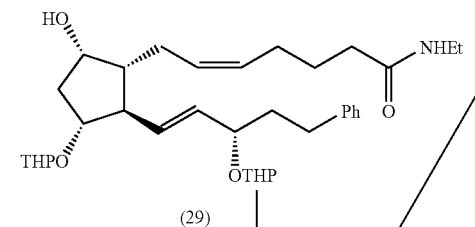
(29)
↓ (i)          ↓ (i)          ↗ (h)
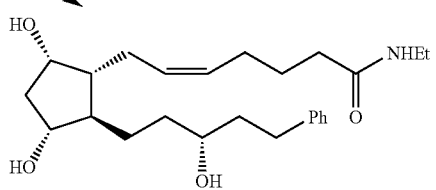
(22)

(a) 1,4 addition of a cuprate reagent formed from compound of formula (IX); (b) stereoselective reduction; (c) protection with a hydroxyl protecting group; (d) dihydroxylation; (f) diol cleavage; (g) Wittig reaction: (h) amidation; (i) deprotection.
The present invention further provides methods for synthesising Travoprost as shown in Scheme 4:
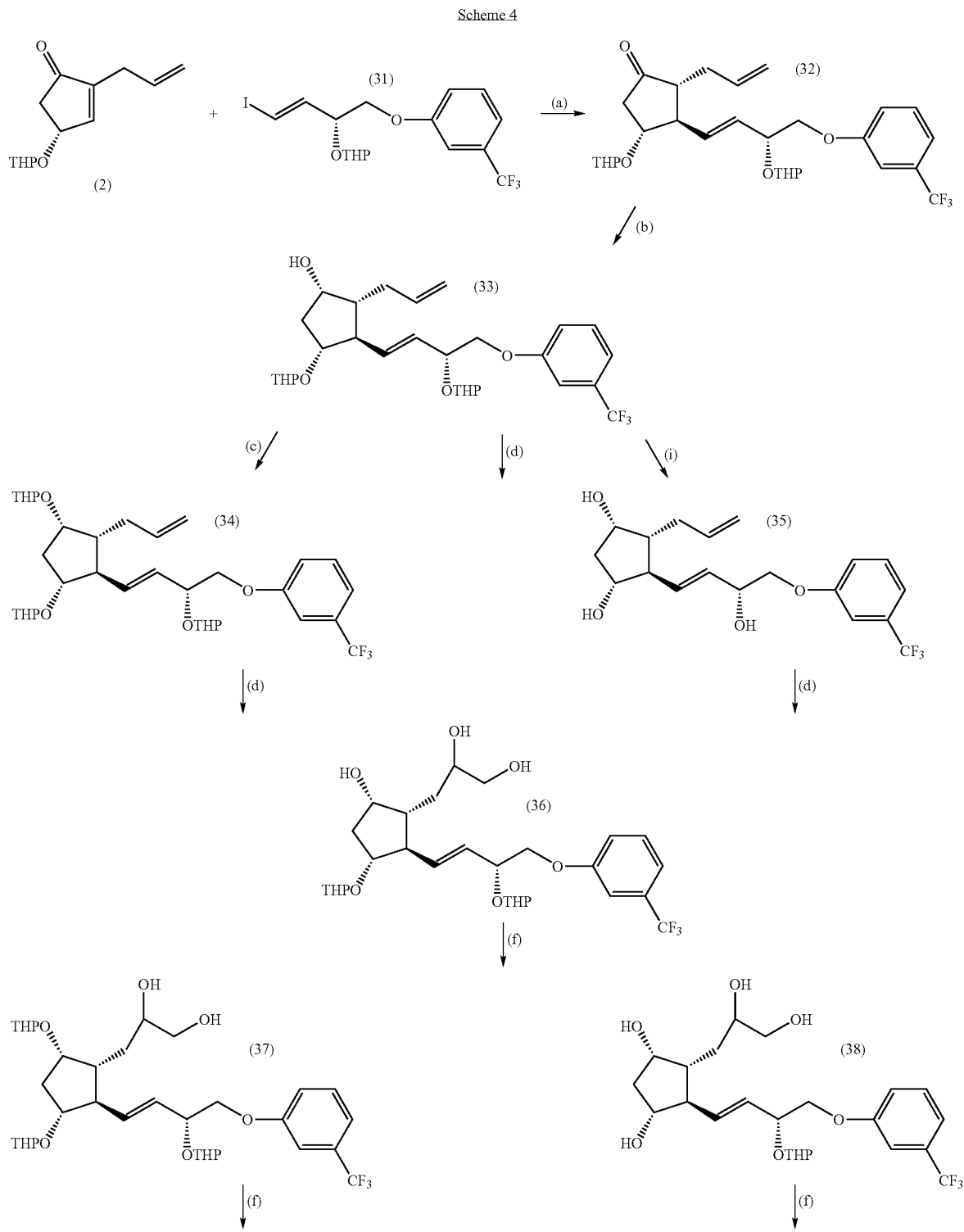

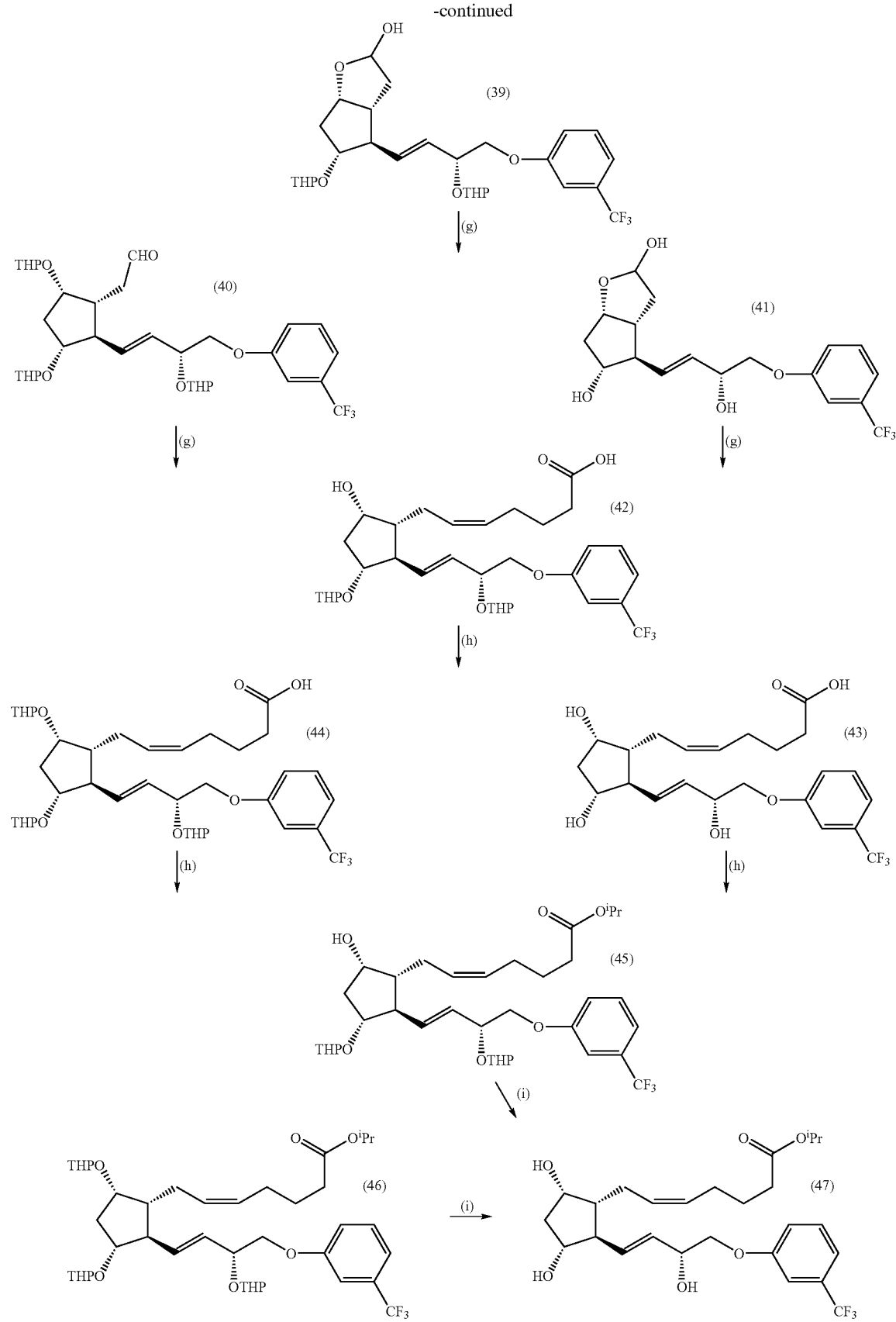

(a) 1,4 addition of a cuprate reagent formed from compound of formula (IX); (b) stereoselective reduction; (c) protection with a hydroxyl protecting group; (d) dihydroxylation; (f) diol cleavage; (g) Wittig reaction: (h) esterification; (i) deprotection.

The invention will now be described by reference to examples which are not intended to be limiting of the invention:

Synthesis of Vinyl Iodide (1)

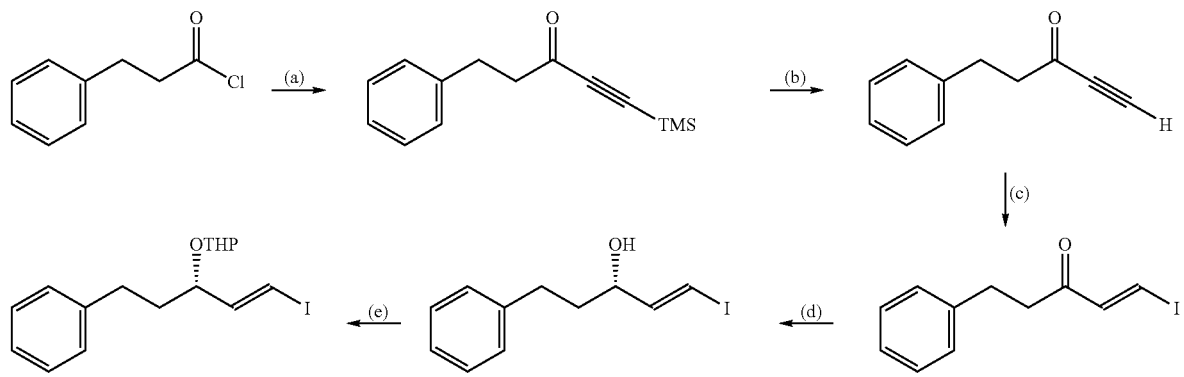

Step (a): A 5 l, three-necked round bottom flask equipped with a mechanical stirrer, a dropping funnel, a cooling bath and an internal temperature probe was charged with $AlCl_3$ (217.48 g, 1.63 mole, 1.1 eq.) and $CH_2Cl_2$ (1 l) under $N_2$ atmosphere. The reaction mixture was cooled using ice/salt/methanol bath while the agitation was initiated. Once the temperature was $\leq -10°$ C., a solution of 3-phenylpropionyl chloride (Aldrich, 250 g, 1.48 mole, 1 eq.) and bis(trimethylsilyl)acetylene (GFS Chemicals, 278 g, 1.63 mole, 1.1 eq.) in $CH_2Cl_2$ (1 l) was added slowly via addition funnel keeping the temperature $\leq 0°$ C. throughout the addition. Upon completion of the addition, the cooling bath was removed and the mixture was allowed to warm to RT with agitation. After ~0.5 h, the reaction was monitored by TLC for completion. Upon completion of the reaction (ca. 20 min), the mixture was poured slowly to phosphate buffer (pH ~7, 4 l) with agitation. The organic layer was separated and the aqueous layer was extracted with $CH_2Cl_2$ (500 ml). The organic layers were combined, washed with 10% aq. NaCl (2×750 ml), dried over anhydrous $MgSO_4$ (500 g), filtered and the solvent was removed in vacuo to produce a dark oil. The oil was further dried under high vacuum at RT for ~18 h.

Step (b): A 12 l, three-necked round bottom flask equipped with a mechanical stirrer and a dropping funnel was charged with the oil produced in step (a) (316 g, 1.37 mole, 1 eq.) and methanol (3 l). To this was added 0.00M $Na_2B_4O_7.10H_2O$ (11.44 g in 3 l of $H_2O$) slowly via addition funnel with agitation. The mixture was stirred at room temperature. The progress of the reaction was monitored by TLC. Upon completion of the reaction (ca. 30 min), the pH of the reaction mixture was adjusted to ~3 (pH paper) using 1N HCl (82.6 ml). The solvent was removed in vacuo and the aqueous layer was extracted with $CH_2Cl_2$ (3×500 ml). The organic layers were combined, washed with brine solution (500 ml), dried over anhydrous $MgSO_4$, filtered and the solvent was removed in vacuo to give a dark viscous oil. The oil was passed through a plug of silica gel (550 g) using 2.5% EtOAc/Heptane (v/v, 5 L) as an eluent.

Step (c): A 5 l three-necked round bottom flask equipped with a mechanical stirrer, a dropping funnel and an internal temperature probe was charged with the oil produced in step (b) (121.36 g, 0.77 mole, 1 eq.), NaI (117.42 g, 0.78 mole, 1.02 mole), n-Bu$_4$NI (28.4 g, 0.077 mole, 10 mole %) and MTBE (1213 ml). The agitation was initiated. To this was slowly added 4M $H_2SO_4$ (348 g) via addition funnel with agitation. After ~0.5 h, additional amount of 4M $H_2SO_4$ (174 g) was added. The completion of the reaction was monitored by TLC. Upon completion of the reaction (ca 4.5 h), the reaction mixture was transferred to a 4 l separatory funnel. The organic layer was separated and the aqueous layer was extracted with MTBE (500 ml). The organic layers were combined and washed with 5% aq. $NaHCO_3$ (2×750 ml), saturated brine (750 ml), dried over $MgSO_4$ (300 g), filtered and the solvent was removed in vacuo to produce a brown red viscous oil. The oil was passed through a pad of silica gel (600 g) using 2.5% EtOAc/Heptane (v/v, 6 L) to give a viscous oil, which was further dried under high vacuum for ~18 h at RT.

Step (d): A 1 l three-necked round bottom flask equipped with a cooling bath, a magnetic stirrer, a $N_2$ inlet and an internal temperature probe was charged with the oil produced in step (c) (35 g, 0.12 mole, 1 eq.), dry toluene (350 ml) and R-2-methyl-CBS-oxazoborolidine (Callery Chemicals, 24.47 ml, 20 mole %, 1M solution in toluene). The mixture was cooled in an acetone-dry ice bath to −78° C. (internal temperature) with stirring, and a solution of catecholborane (Callery Chemicals, 29.34 g, 0.25 mole, 2 eq.) in dry toluene (260 ml) was added over a period of 8 to 9 hours via a syringe pump. Upon completion of the addition, the reaction flask was kept in the bath, and the reaction mixture was allowed to warm slowly to RT overnight. TLC analysis showed that the reaction was complete. The mixture was cooled to $\leq 10°$ C. (salt/ice bath) and methanol (150 ml) was added slowly. The mixture was allowed to warm to room temperature (~20° C.) and 4 N NaOH solution (165 ml) was added. The biphasic solution was allowed to stir at room temperature for ~45 minutes and then transferred to a separatory funnel. The organic layer was separated and the aqueous layer was back washed with toluene (100 ml). The organic layers were combined and washed with 4 N HCl (2×150 ml), saturated brine solution (250 ml), dried over $MgSO_4$ (100 g), filtered and the solvent was removed in vacuo to give a viscous oil which solidified upon standing at RT. The crude product was purified by silica gel chromatography (250 g) using 5% EtOAc-heptane (v/v). The product was obtained as a solid (30 g), which was further triturated with heptane (60 mL) at room temperature to give an off-white solid. The solid was suction filtered and dried under high vacuum at room temperature for ~16 h.

Step (e): The hydroxy group of the product of step (d) was protected using 3,4-dihydro-2H-pyran and standard techniques.

Synthesis of Cyclopentenone (2)

charged with the above enone mixture (456 g), toluene (3.5 l), triethylamine (367.3 g, 3.6 mol), and anhydrous tribromoacetaldehyde (92.65 g, 0.33 mol). The resulting mixture was allowed to stir at room temperature for 21 h, and diluted with water (3 l). The layers were separated, and the aqueous layer was extracted with ethyl acetate (3×0.75 l). The combined organic layers were washed with 25% wt/v brine solution (2 l) and dried over MgSO$_4$. The drying agent was filtered off and the filtrate was concentrated under reduced pressure to give a dark viscous oil (415 g). The oil was

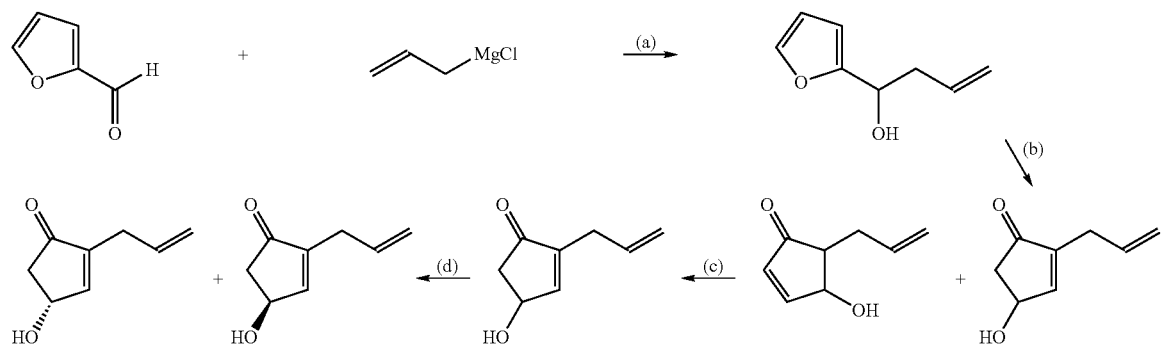

Step (a): A 22 l 3-necked round bottom flask equipped with an overhead mechanical stirrer, a temperature probe, and an addition funnel was purged with nitrogen and charged with a 2M solution of allylmagnesium chloride in THF (8 l, 16 mol). The flask was cooled in an ice bath to bring the internal temperature to 5° C. A solution of 2-furaldehyde (1.2 kg, 12.5 mol) in anhydrous THF (2 l) was added to the Grignard solution slowly over 4.75 h maintaining the internal temperature below 12° C. TLC analysis after 15 min indicated that the reaction was complete. The reaction was quenched by the sequential addition of saturated NH$_4$Cl (4 l), water (2 l), and concentrated HCl (1.4 l). The layers were separated, and the aqueous layer was extracted with ethyl acetate (3 l). The combined organic layers were washed with brine (800 g of NaCl dissolved in 3 l of water), and concentrated on a rotary evaporator to give the addition product as a dark coloured oil (2.1 kg), which was used without further purification. $^1$H NMR spectrum conformed to structure.

Step (b): A 22 l 3-necked round bottom flask equipped with an overhead mechanical stirrer, a temperature probe, and a heating mantle was charged with a buffered solution with a pH of 4.80. A solution of the product of step (a) (500 g, 2.9 mol) in 1,4-dioxane (1.5 l) was added in one portion, and the mixture was heated to around 95° C. over a 5.5 h period. The reaction mixture was stirred at this temperature for ca. 60 h, at which time TLC analysis indicated near complete consumption of the step (a) product. The reaction mixture was allowed to cool to 50° C., and solid NaCl (6 kg) was added with stirring. The resulting solution was extracted with ethyl acetate (1×3 l and 1×2 l), and the combined organic phases were dried over MgSO$_4$. The drying agent was filtered off, and the filtrate was concentrated under reduced pressure. The residual oil was co-evaporated with toluene (250 ml) and dried under high vacuum to give a reddish brown viscous oil (456 g).

Step (c): A 5 l 3-necked round bottom flask equipped with an overhead mechanical stirrer, and a nitrogen inlet was chromatographed on silica gel (1 kg) eluting with 15:85 ethyl acetate-heptane (7 l), 30:70 ethyl acetate-heptane (2 l), and 50:50 ethyl acetate-heptane (5 l) to give an enone as an oil (199 g, 50% yield).

Step (d): The enone prepared in step (c) was resolved by Simulated Moving Bed chiral chromatography (SMB). The desired R-enantiomer was obtained in >99% optical purity.

To form the cyclopentenone (2), the alcohol of the R-enantiomer formed in step (d) was protected using 3,4-dihydro-2H-pyran and standard techniques.

EXAMPLE 1

1,4 Addition of a Cuprate Reagent Formed from a Compound of Formula (IX)

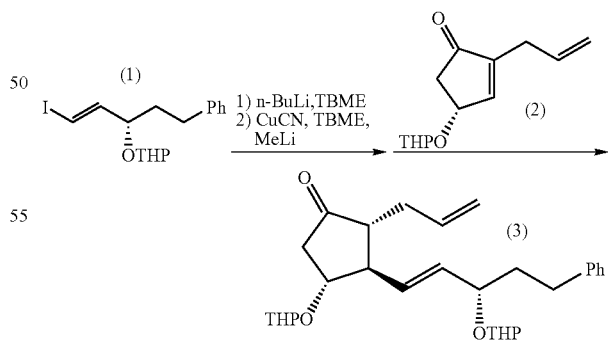

A dry 250 ml 3-necked round bottom flask equipped with a magnetic stirring bar, a temperature probe, and rubber septa, was purged with nitrogen. The flask was charged with a solution of vinyl iodide (1) (8.43 g, 22.65 mmol) in tert-butyl methyl ether (TBME, 40 ml) and cooled in an acetone-dry ice bath. A solution of n-butyllithium in hexanes (2.517M, 9.5 ml, 23.8 mmol) was added, and the mixture was stirred at −78° C. for 2 h.

A dry 1 l 3-necked round bottom flask equipped with a magnetic stirring bar, a temperature probe, and rubber septa, was purged with nitrogen and charged with solid cuprous cyanide (2.12 g, 23.78 mmol). Anhydrous TBME (60 ml) was added and the flask was cooled to −78° C. in an acetone-dry ice bath. A solution of methyllithium in THF-cumene (1M, 23.78 ml, 23.78 mmol) was slowly added to the stirring suspension. After the addition was complete, the flask was placed in an ice bath and the contents stirred for 30 min giving a clear solution. The cuprate solution was cooled again to −78° C., and the vinyl lithium solution was added from the 250 ml flask via cannula. The resulting yellow solution was quickly warmed to −40° C., stirred for 20 min, and recooled to −78° C. A solution of cyclopentenone (2) (2.52 g, 11.34 mmol) in anhydrous TBME (30 ml) was added by cannula, and the mixture was stirred at −78° C. for 30 min. The reaction flask was removed from the cooling bath, and the reaction was quenched by the careful addition of saturated NH$_4$Cl (15 ml). The layers were separated and the organic layer was washed with 1:9 NH$_4$OH—NH$_4$Cl (2×200 ml). The combined aqueous washes were back extracted with TBME (100 ml). The combined organic layers were washed with saturated brine (100 ml), dried (Na$_2$SO$_4$), filtered and concentrated to give a pale yellow oil (22.80 g). The oil was chromatographed on silica gel (200 g) eluting with 1:9 ethyl acetate-heptane (1 l) and 1.5:8.5 ethyl acetate-heptane (3 l) to give the pure product (3) (4.15 g, 78.6% yield). $^1$H NMR conformed to structure.

EXAMPLE 2

Stereoselective Reduction

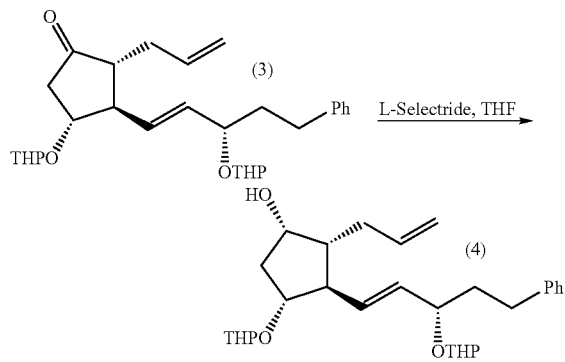

A dry 250 ml 3-necked round bottom flask equipped with a magnetic stirring bar, a temperature probe, and an addition funnel, was purged with nitrogen. The flask was charged with a solution of L-Selectride in THF (1M, 16.25 ml, 16.25 mmol) and cooled to −78° C. in an acetone-dry ice bath. A solution of (3) (3.80 g, 8.13 mmol) in anhydrous THF (60 ml) was added slowly from the addition funnel over 35 min, and the mixture was stirred at −78° C. for 4.5 h. TLC analysis indicated that the reaction was complete. The cooling bath was removed, and the mixture was quenched by the addition of 30% hydrogen peroxide (2.2 ml, 19.4 mmol) followed by saturated NH$_4$Cl (50 ml). Ethyl acetate (200 ml) was added and the layers were separated. The aqueous layer was extracted with ethyl acetate (200 ml). The combined organic layers were washed with 10% sodium bisulfite (50 ml), dried (Na$_2$SO$_4$), filtered and concentrated to give the crude product (5.05 g). This material was chromatographed on silica gel (75 g) eluting with 1:9 ethyl acetate-heptane and 3:7 ethyl acetate-heptane to give the pure product (4) (3.25 g, 85.1% yield). $^1$H NMR conformed to structure.

EXAMPLE 3a

Selective Dihydroxylation

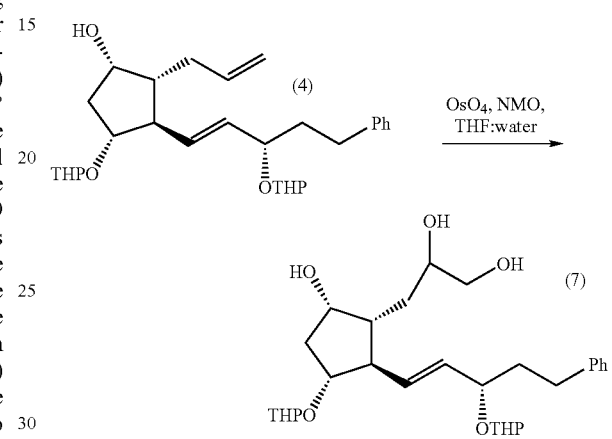

A solution of alkene (4) (2.5 g, 5.3 mmol) in THF (20 ml) was cooled to −9° C. and a solution of N-methylmorpholine oxide monohydrate (NMO, 1.6 g, 11.7 mmol) in water (4 ml) was added. A solution of osmium tetroxide (60 mg, 0.236 mmol) in water (1.5 ml) was added slowly while keeping the reaction temperature below −7° C. After the addition was complete, the reaction mixture was stirred at −7 to −5° C. for 4 h. The reaction was quenched by the addition of solid sodium bisulfite (1.5 g), the mixture stirred for 5 min, and filtered through a bed of celite. The filter cake was washed with ethyl acetate, and the combined filtrate was washed with saturated aqueous sodium bicarbonate and water. The organic layer was dried (Na$_2$SO$_4$), filtered and concentrated to give the crude product as a dark brown oil. This oil was chromatographed on silica gel (50 g) eluting with 1:99 methanol-dichloromethane and 5:95 methanol-dichloromethane to give the pure triol (7) as a yellow oil (2.3 g, 86.8% yield). $^1$H NMR conformed to structure.

EXAMPLE 3b

Selective Dihydroxylation

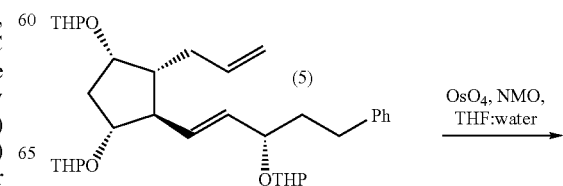

-continued

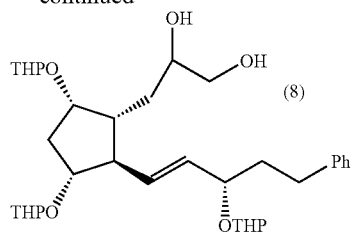

A solution of alkene (5) (11.37 g, 20.17 mmol) in THF (100 ml) was cooled to −9° C. and a solution of N-methylmorpholine oxide monohydrate (NMO, 6.84 g, 50.42 mmol) in water (20 ml) was added. A solution of osmium tetroxide (256 mg, 1.010 mmol) in water (6.42 ml) was added slowly while keeping the reaction temperature below −6.5° C. After the addition was complete, the reaction mixture was stirred at −10 to −7.8° C. for 4 h. The reaction was quenched by the addition of solid sodium bisulfite (6.84 g), the mixture stirred for 5 min, and filtered through a bed of celite. The filter cake was washed with ethyl acetate (200 ml), and the combined filtrates were washed with saturated aqueous sodium bicarbonate and water. The organic layer was dried ($Na_2SO_4$), filtered and concentrated to give the crude product as a dark brown oil. This oil was chromatographed on silica gel (140 g) eluting with 70:30 ethyl acetate-heptane, ethyl acetate, and 2:98 methanol-ethyl acetate to give the pure diol (8) (8.70 g, 72.1% yield). $^1H$ NMR spectrum conformed to structure.

EXAMPLE 4a

Reduction

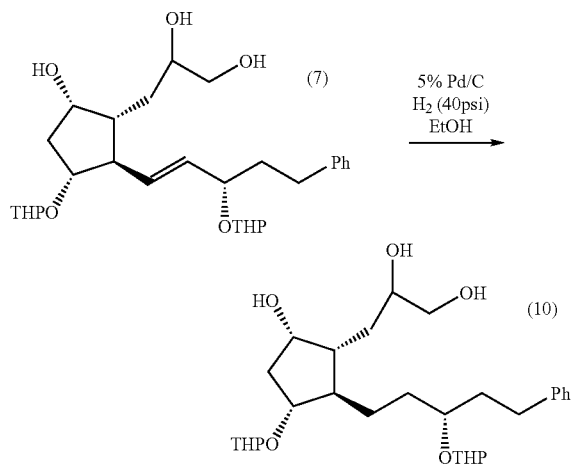

A solution of alkene (7) (2.3 g, 4.6 mmol) in ethanol (200 ml) and 5% palladium on activated carbon (contains 50–60 wt % water, 300 mg) was stirred under 40 psi of hydrogen for 4 h. A fresh charge of catalyst (200 mg) was added and the hydrogenation continued for 8 h. $^1H$ NMR analysis indicated complete reduction of the double bond. The reaction mixture was filtered through a bed of celite and the filtrate was concentrated to give triol (10) as an oil (2.1 g, 91.3% yield).

EXAMPLE 4b

Reduction

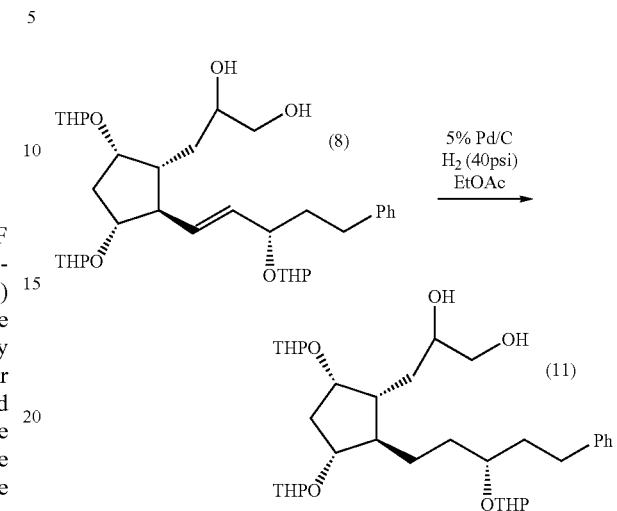

A solution of alkene (8) (9.32 g, 15.59 mmol) in ethyl acetate (200 ml) and 5% palladium on activated carbon (contains 50–60 wt % water, 11.0 g) was stirred under 45 psi of hydrogen for 18 h. A fresh charge of catalyst (0.5 g) was added and the hydrogenation continued for 2 days. A second charge of fresh catalyst (0.5 g) was added and the hydrogenation continued for 1 day. $^1H$ NMR analysis indicated that the double bond was not completely reduced. The reaction mixture was filtered, concentrated to dryness, the residue dissolved in ethanol (200 ml), and hydrogenated over 5% palladium on activated carbon (0.5 g, 40 psi of hydrogen) for 24 h. The reaction mixture was filtered through a bed of celite and the filtrate was concentrated to give diol (11) as a colourless oil (8.40 g, 89.8% yield).

EXAMPLE 5a

Diol Cleavage

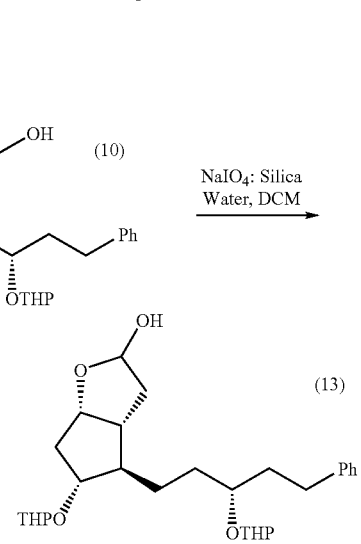

A mixture of sodium periodate (1.90 g, 8.14 mmol), silica gel (2.00 g) and water (2 ml) were stirred until a free flowing powder was obtained. This powder was added in one portion to a solution of triol (10) (2.10 g, 4.14 mmol) in dichloromethane (25 ml) and the mixture was stirred at room temperature for 2 h. The solids were removed by filtration through a short pad of Na$_2$SO$_4$ (5 g), and the filtrate was concentrated to dryness. The crude product was chromatographed on silica gel (30 g) eluting with 20:80 ethyl acetate-heptane to give the product (13) as an oil which solidified slowly on storage (1.65 g, 83.8% yield). $^1$H NMR conformed to structure.

EXAMPLE 5a

Diol Cleavage

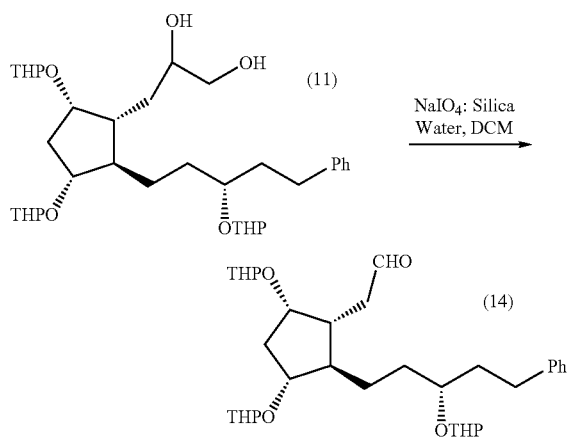

A mixture of sodium periodate (5.00 g, 23.38 mmol), silica gel (5.00 g) and water (5 ml) were stirred until a free flowing powder was obtained. This powder was added in one portion to a solution of diol (11) (7.00 g, 11.69 mmol) in dichloromethane (50 ml) and the mixture was stirred at room temperature for 3 h. The solids were removed by filtration through a short pad of Na$_2$SO$_4$ (10 g), and the filtrate was concentrated to dryness. The crude product was chromatographed on silica gel (55 g) eluting with 15:85 ethyl acetate-heptane to give aldehyde (2.25 g, 33.9% yield). $^1$H NMR spectrum conformed to structure.

EXAMPLE 6a

Wittig Olefination

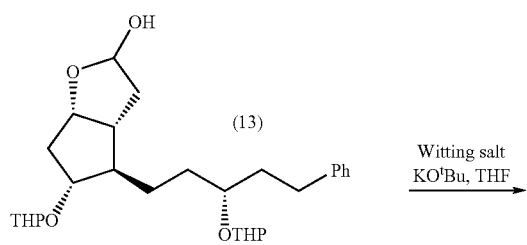

-continued

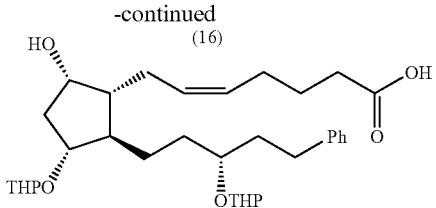

A dry 250 ml 3-necked round bottom flask equipped with a magnetic stirring bar, a temperature probe, and rubber septa, was purged with nitrogen. The flask was charged with solid 4-carboxybutylphosphonium bromide (3.67 g, 8.27 mmol) and anhydrous THF (20 ml), and cooled to −12° C. in an ice-methanol bath. A solution of potassium tert-butoxide (1.86 g, 16.54 mmol) in anhydrous THF (20 ml) was added by syringe keeping the internal temperature below −9° C. The resulting orange-red suspension was stirred for 1 h between −9° C. and −12° C. A solution of the lactol (13) (1.60 g, 3.39 mmol) in anhydrous THF (20 ml) was added by syringe keeping the temperature below −6° C. The resulting suspension was stirred in the cold for 2 h, and quenched by the addition of water (50 ml). The THF was removed under reduced pressure and TBME (100 ml) was added to the residue. The layers were separated, and the organic layer was washed with 6% aqueous sodium chloride (60 ml). The combined aqueous layers were acidified to pH 4.0 with 5% aqueous citric acid, and extracted with ethyl acetate (2×100 ml). The combined ethyl acetate extracts were washed with water (100 ml), dried (Na$_2$SO$_4$), filtered and concentrated to a colorless syrup (1.90 g) which was carried forward without further purification. $^1$H NMR showed that this syrup is a mixture of acid (16) and unreacted Wittig salt.

EXAMPLE 6b

Wittig Olefination

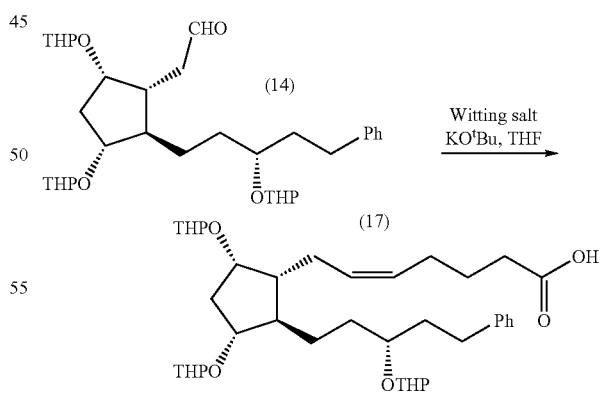

A dry 250 ml 3-necked round bottom flask equipped with a magnetic stirring bar, a temperature probe, and rubber septa, was purged with nitrogen. The flask was charged with solid 4-carboxybutylphosphonium bromide (3.51 g, 7.93 mmol) and anhydrous THF (100 ml), and cooled to −10° C. in an ice-methanol bath. A solution of potassium tert-butoxide (1.78 g, 15.85 mmol) in anhydrous THF (10 ml) was added by syringe. The resulting orange-red suspension was stirred for 1 h at 0° C., cooled to −10° C., and a solution of aldehyde (14) (2.25 g, 3.96 mmol) in anhydrous THF (15 ml) was added by syringe. The resulting suspension was stirred in the cold for 2 h, and quenched by the addition of water (50 ml). The THF was removed under reduced pressure and the mixture was washed with TBME (2×70 ml). The combined organic layers were extracted with water (50 ml). The combined aqueous layers were acidified to pH 3.0 with 5% aqueous citric acid, and extracted with ethyl acetate (2×100 ml). The combined ethyl acetate extracts were dried (Na$_2$SO$_4$), filtered and concentrated to crude acid (17) (3.30 g) which was carried forward without further purification.

EXAMPLE 7a

Esterification

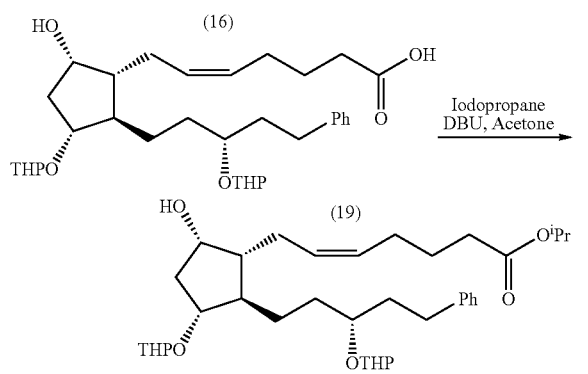

The crude olefination product from example 6a (1.84 g) was dissolved in acetone (20 ml), and the solution was cooled in an ice bath. The solution was treated with 1,8-diazabicyclo[5.4.0]undec-7-ene (DBU, 2.02 g, 19.86 mmol), and 2-iodopropane (3.38 g, 13.24 mmol), and allowed to stir at room temperature under an atmosphere of nitrogen for 16 h. The reaction mixture was concentrated, and the residue was partitioned between ethyl acetate (100 ml) and 5% aqueous citric acid (50 ml). The layers were separated, the organic layer was washed with saturated aqueous sodium bicarbonate (20 ml), and dried (Na$_2$SO$_4$). The drying agent was filtered off and the filtrate was concentrated to dryness. The residue was chromatographed on silica gel (30 g) eluting with 15:85 ethyl acetate-heptane to give pure ester (19) (1.41 g, 69.2% yield from lactol (13)). $^1$H NMR conformed to structure.

EXAMPLE 7b

Esterification

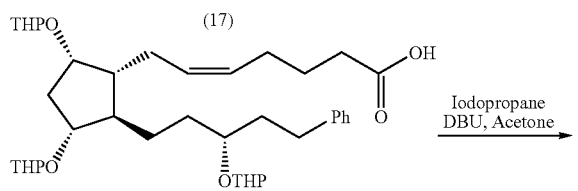

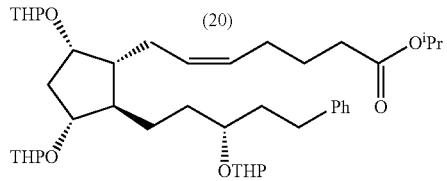

The crude olefination product from example 6b (3.30 g) was dissolved in acetone (30 ml), and the solution was cooled in an ice bath. The solution was treated with 1,8-diazabicyclo[5.4.0]undec-7-ene (DBU, 2.85 g, 18.72 mmol), and 2-iodopropane (4.77 g, 28.06 mmol), and allowed to stir at room temperature under an atmosphere of nitrogen for 64 h. A voluminous precipitate formed. The reaction mixture was concentrated, and the residue was partitioned between ethyl acetate (170 ml) and 5% aqueous citric acid (75 ml). The layers were separated, the organic layer was washed with water (75 ml), saturated aqueous sodium bicarbonate (75 ml), and dried (Na$_2$SO$_4$). The drying agent was filtered off and the filtrate was concentrated to dryness. The residue was chromatographed on silica gel (30 g) eluting with 15:85 ethyl acetate-heptane to give pure ester (20) (2.18 g, 80.7% yield from aldehyde (14)). $^1$H NMR spectrum conformed to structure.

EXAMPLE 8a

Deprotection

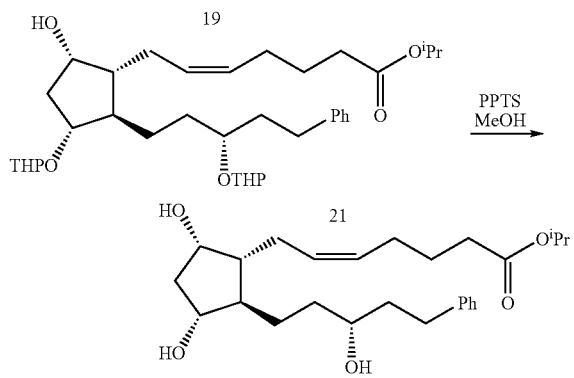

To a solution of ester (19) (1.41 g, 2.35 mmol) in methanol (20 ml) was added pyridinium p-toluenesulfonate (PPTS, 30 mg, 0.12 mmol), and the mixture was heated in an oil bath that was maintained at 52° C. for 4 h. TLC indicated that all the starting material was consumed. Solid sodium bicarbonate (50 mg) was added to the reaction mixture and the solvent was removed under reduced pressure. The residue was chromatographed on silica gel (30 g) eluting with 30:70 ethyl acetate-heptane (11), 50:50 ethyl acetate-heptane (11 L), and 65:35 ethyl acetate-heptane (1.51) to give Latanoprost (21) as a colorless oil (910 mg, 90.0% yield). $^1$H NMR conformed to structure.

EXAMPLE 8b

Deprotection

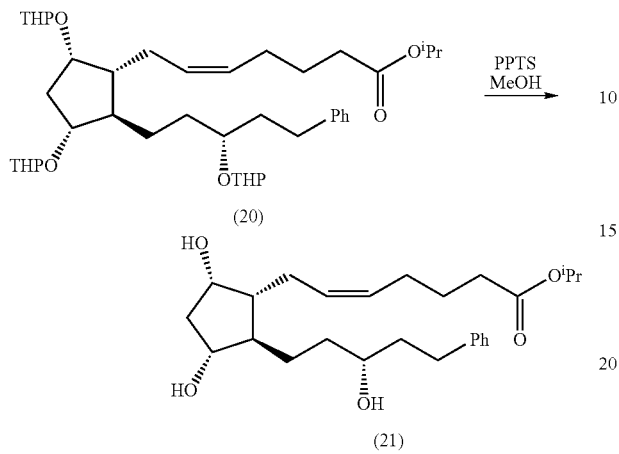

To a solution of ester (20) (2.15 g, 3.15 mmol) in methanol (40 mL) was added pyridinium p-toluenesulfonate (PPTS, 10 mg, 0.04 mmol), and the mixture was heated in an oil bath that was maintained at 45° C. for 6 h. TLC indicated that all the starting material was consumed. Solid sodium bicarbonate (200 mg) was added to the reaction mixture and the solvent was removed under reduced pressure. The residue was partitioned between ethyl acetate (150 ml) and water. The layers were separated and the organic phase was washed with saturated sodium bicarbonate (25 ml), and water (25 ml). The solvent was removed and the residue was chromatographed on silica gel (40 g) eluting with 35:65 ethyl acetate-heptane (11), and 50:50 ethyl acetate-heptane (11) to give Latanoprost (21) as a colorless oil (1.14 g, 83.7% yield). $^1$H NM spectrum conformed to structure.

Although the invention is illustrated and described herein with reference to specific embodiments, the invention is not intended to be limited to the details shown. Rather, various modifications may be made in the details within the scope and range of equivalents of the claims without departing from the invention.

What is claimed is:

1. A process for synthesising Latanoprost comprising the steps of:

a) preparing a compound of formula (3):

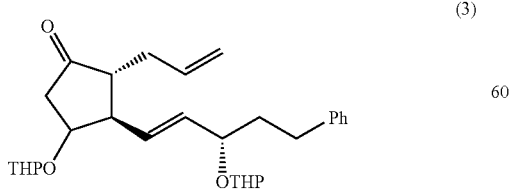

said preparing comprising converting a compound of formula (1):

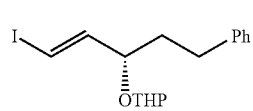

to a cuprate reagent and performing a 1,4 addition reaction between the cuprate reagent and a compound of formula (2):

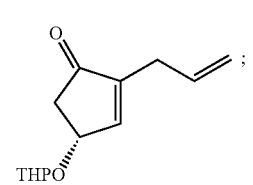

b) selectively reducing the compound of formula (3) to provide a compound of formula (4):

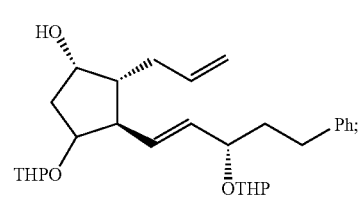

c) dihydroxylating the compound of formula (4) to provide a compound of formula (7):

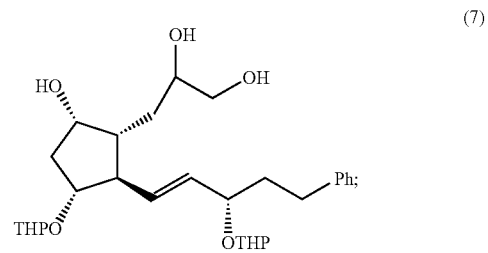

d) reducing the compound of formula (7) to provide a compound of formula (10):

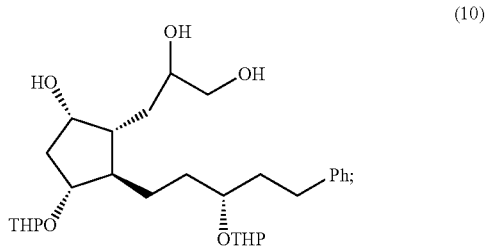

e) performing a diol cleavage reaction on the compound of formula (10) to provide a compound formula (13):

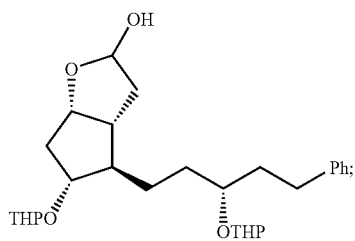
(13)

f) performing a Wittig reaction on the compound of formula (13) to provide a compound of formula (16):

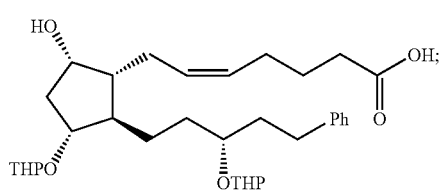
(16)

g) esterifying the compound of formula (16) to provide a compound of formula (19):

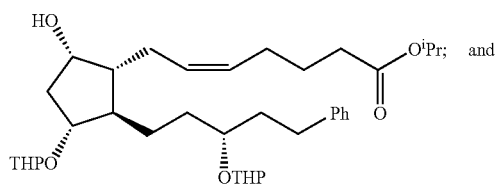
(19)

h) deprotecting the compound of formula (19) to provide Latanoprost.

2. A process for synthesising Latanoprost comprising the steps of:

a) preparing a compound of formula (3):

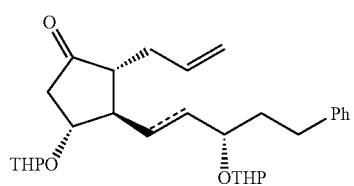
(3)

said preparing comprising converting a compound of formula (1):

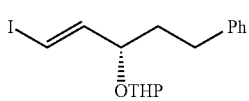
(1)

to a cuprate reagent and performing a 1,4 addition reaction between the cuprate reagent and a compound of formula (2):

(2)

b) selectively reducing the compound of formula (3) to provide a compound of formula (4):

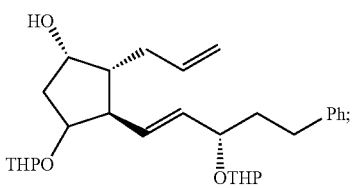
(4)

c) protecting the compound of formula (4) to provide a compound of formula (5):

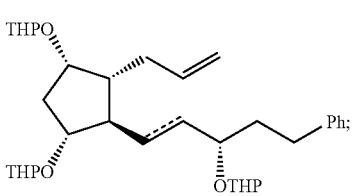
(5)

d) dihydroxylating the compound of formula (5) to provide a compound of formula (8):

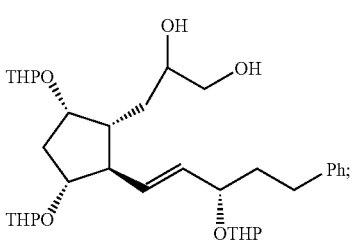
(8)

e) reducing the compound of formula (8) to provide a compound of formula (11):

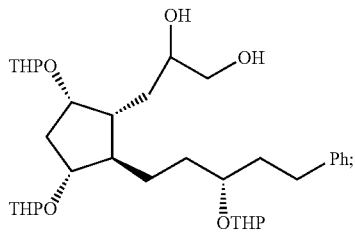
(11)

f) performing a diol cleavage reaction on the compound of formula (11) to provide a compound of formula (14):

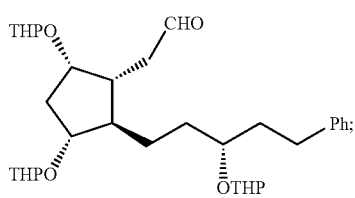
(14)

g) performing a Wittig reaction on the compound of formula (14) to provide a compound of formula (17):

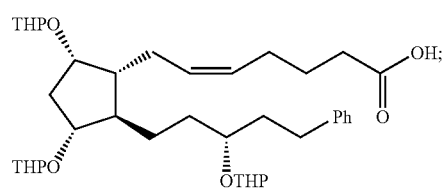
(17)

h) esterifying the compound of formula (17) to provide a compound of formula (20):

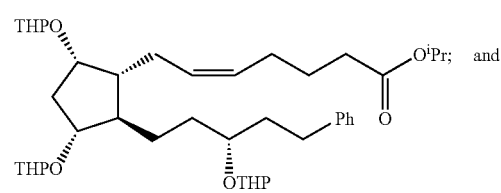
(20)

i) deprotecting the compound of formula (20) to provide Latanoprost.

3. A process for synthesising Latanoprost comprising the steps of:

a) preparing a compound of formula (3):

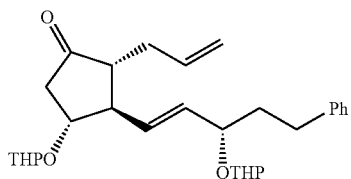
(3)

said preparing comprising converting a compound of formula (1):

(1)
I⁀⁀⁀Ph, OTHP to a cuprate reagent and performing a 1,4 addition reaction between the cuprate reagent and a compound of formula (2):

(2)

b) selectively reducing the compound of formula (3) to provide a compound of formula (4):

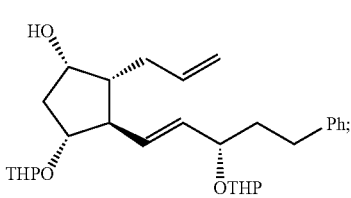
(4)

c) deprotecting the compound of formula (4) to provide a compound of formula (6):

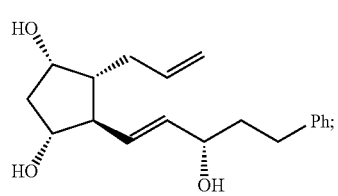
(6)

d) dihydroxylating the compound of formula (6) to provide a compound of formula (9):

e) reducing the compound of formula (9) to provide a compound of formula (12):

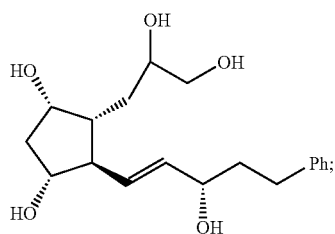
(9)

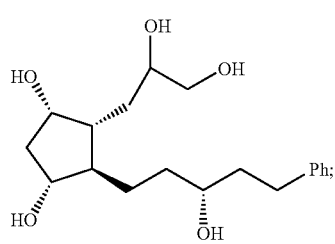
(12)

f) performing a diol cleavage reaction on the compound of formula (12) to provide a compound of formula (15):

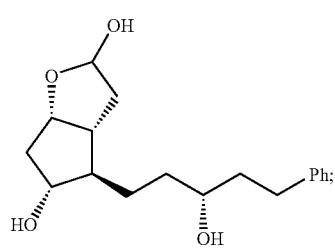
(15)

g) performing a Wittig reaction on the compound of formula (15) to provide a compound of formula (18):

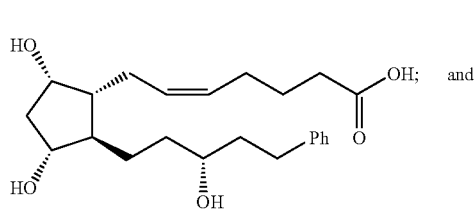
(18)

h) esterifying the compound of formula (18) to provide Latanoprost.

4. A process for the preparation of a prostaglandin compound having the formula (I):

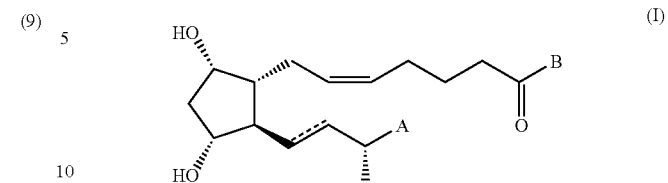
(I)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR'' and NHR'' wherein R'' is $C_1$–$C_6$ alkyl groups; and

- - - - - represents a double bond or a single bond;
the process comprising a step of preparing a compound of formula (VIII):

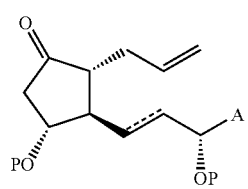
(VIII)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; P is a hydroxyl protecting group; and

- - - - - represents a double bond or a single bond; said step comprising converting a compound of formula (IX):

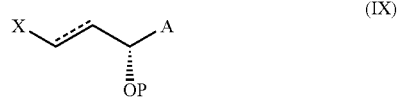
(IX)

wherein A, P and are as defined above and X is a leaving group, to a cuprate reagent and performing a 1,4 addition reaction between the cuprate reagent and a compound of formula (X):

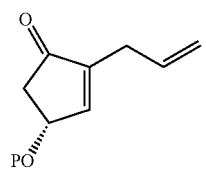

(X)

wherein P is as defined above.

5. A process for the preparation of a prostaglandin compound having the formula (I):

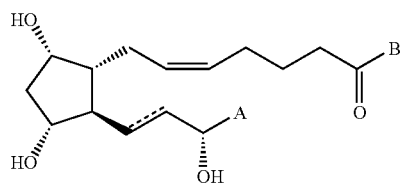

(I)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR" and NHR" wherein R" is $C_1$–$C_6$ alkyl groups; and

- - - - - represents a double bond or a single bond;
the process comprising a step of preparing a compound of formula (VIIa):

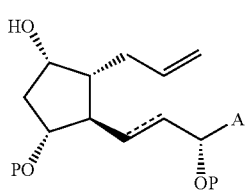

(VIIa)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; P is a hydroxyl protecting group and

- - - - - represents a double bond or a single bond;
said step comprising selectively reducing a compound of formula (VIII):

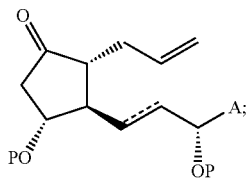

(VIII)

wherein A, P and

- - - - - are as defined above.

6. A process for the preparation of a prostaglandin compound having the formula (I):

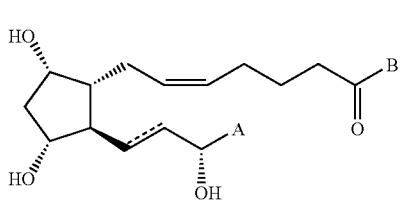

(I)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR" and NHR" wherein R" is $C_1$–$C_6$ alkyl groups; and

- - - - - represents a double bond or a single bond;
the process comprising a step of preparing a compound of formula (VIIb):

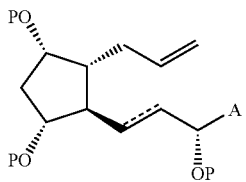

(VIIb)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; P is a hydroxyl protecting group and

----- represents a double bond or a single bond;
said step comprising protecting a compound of formula (VIIa):

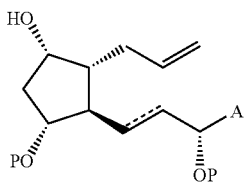

(VIIa)

wherein A, P and

----- are as defined above, with a hydroxyl protecting group.

7. A process for the preparation of a prostaglandin compound having the formula (I):

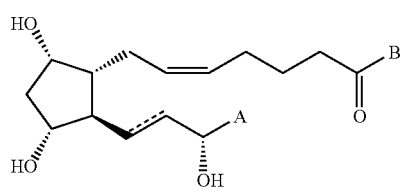

(I)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR" and NHR" wherein R" is $C_1$–$C_6$ alkyl groups; and

----- represents a double bond or a single bond;
the process comprising a step of preparing a compound of formula (VIIc):

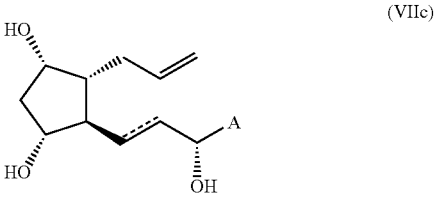

(VIIc)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$ and

----- represents a double bond or a single bond;
said step comprising deprotecting a compound of formula (VIIa):

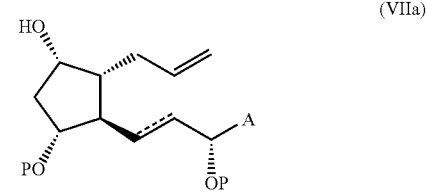

(VIIa)

wherein A and

----- are as defined above and P is a protecting group.

8. A process for the preparation of a prostaglandin compound having the formula (I):

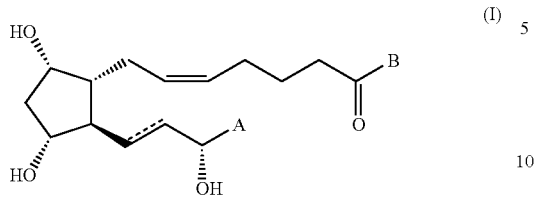
(I)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_n OR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR" and NHR" wherein R" is $C_1$–$C_6$ alkyl groups; and

----- represents a double bond or a single bond;
the process comprising a step of preparing a compound of formula (VIa), (VIb), (VIc), (Va), (Vb) or (Vc):

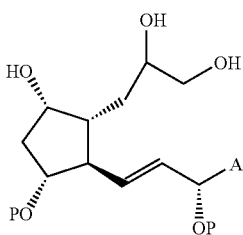
(VIa)

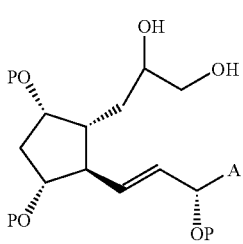
(VIb)

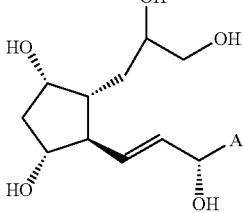
(VIc)

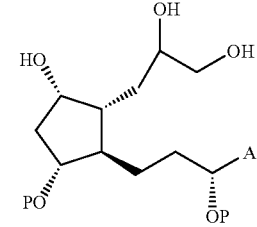
(Va)

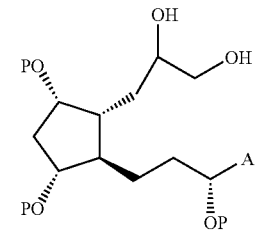
(Vb)

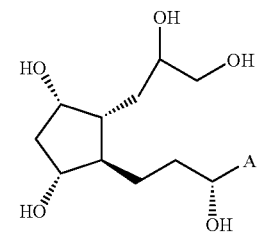
(Vc)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_n OR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; and P is a hydroxyl protecting group;

said step comprising dihydroxylating a compound of formula (VIIa), a compound of formula (VIIb) or a compound of formula (VIIc):

(VIIa)

(VIIb)

-continued

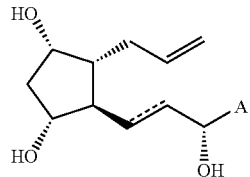
(VIIc)

wherein A and P are as defined above and

- - - - - is a double or single bond.

9. A process for the preparation of a prostaglandin compound having the formula (I):

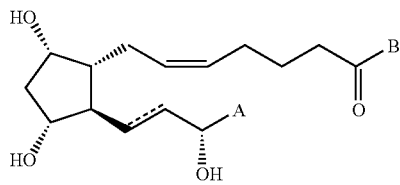
(I)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR" and NHR" wherein R" is $C_1$–$C_6$ alkyl groups; and

- - - - - represents a double bond or a single bond;
the process comprising a step of preparing a compound of formula (Va), (Vb) or (Vc):

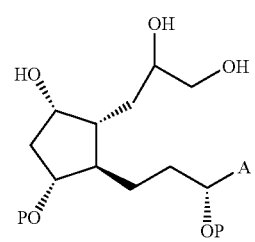
(Va)

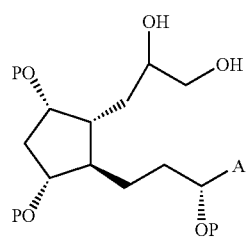
(Vb)

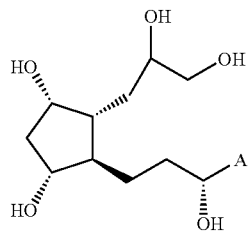
(Vc)

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; and P is a hydroxyl protecting group;

said step comprising reducing a double bond of a compound of formula (VIa), a compound of formula (VIb) or a compound of formula (VIc):

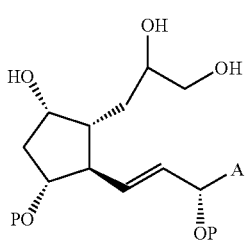
(VIa)

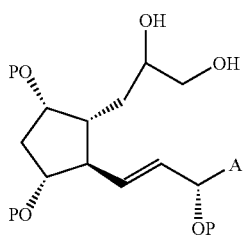
(VIb)

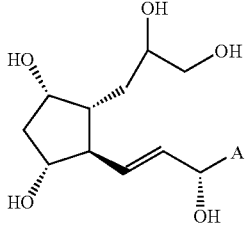
(VIc)

wherein A and P are as defined above.

10. A process for the preparation of a prostaglandin compound having the formula (I):

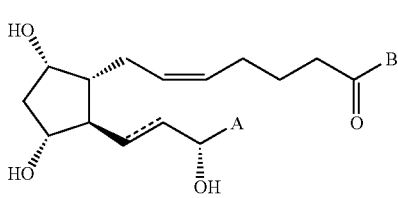

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; B is selected from OR" and NHR" wherein R" is $C_1$–$C_6$ alkyl groups; and

----- represents a double bond or a single bond;
the process comprising a step of preparing a compound of formula (IVa), (IVb) or (IVc):

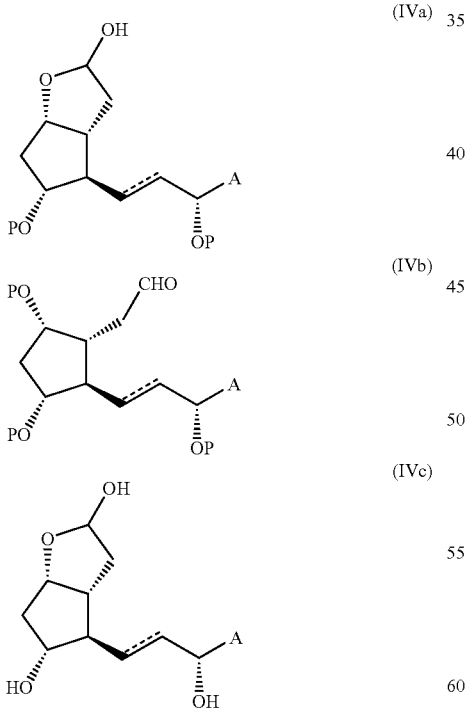

wherein A is selected from the group consisting of $C_1$–$C_6$ alkyl groups; $C_7$–$C_{16}$ aralkyl groups wherein an aryl portion thereof is unsubstituted or substituted with one to three substituents selected from the group consisting of $C_1$–$C_6$ alkyl groups, halo and $CF_3$; and $(CH_2)_nOR'$ wherein n is an integer from 1 to 3 and R' represents a $C_6$–$C_{10}$ aryl group which is unsubstituted or substituted with one to three substituents selected from the group consisting of $C_1$–$C_6$ alkyl groups, halo and $CF_3$; P is a hydroxyl protecting group and

----- represents a double bond or a single bond;
said step comprising performing a diol cleavage reaction on a compound of formula (VIa), (Va), (VIb,), (Vb), (VIc) or (Vc):

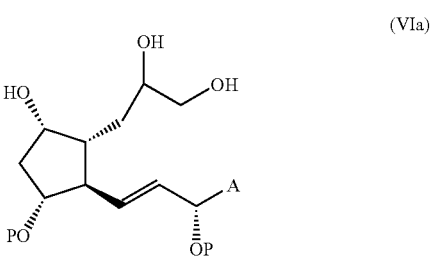

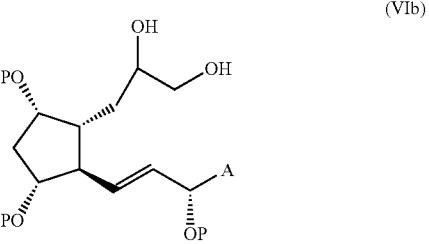

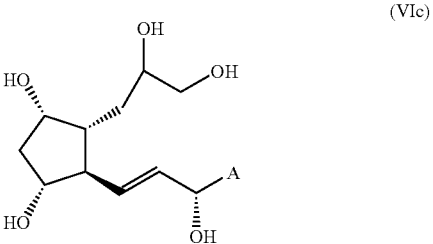

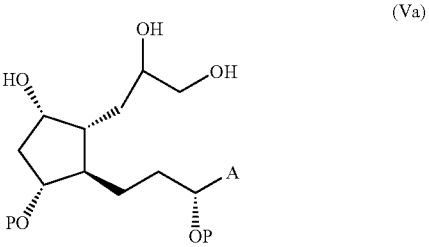

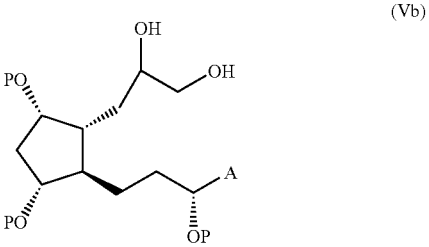

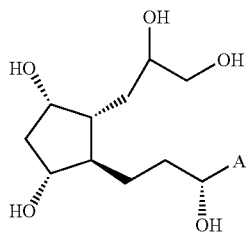
(Vc)

wherein A and P are as defined above.

11. The process according to claim 4, wherein P is a tetrahydropyranyl (THP) protecting group.

12. The process according to claim 4 or claim 11, wherein X is iodine.

13. The process according to claim 4, wherein A is $(CH_2)_2Ph$,

- - - - - represents a double bond, P is THP and X is I.

14. The process according to claim 5, wherein P is a tetrahydropyranyl (THP) protecting group.

15. The process according to claim 5, wherein A is $(CH_2)_2Ph$,

- - - - - represents a double bond and P is THP.

16. The process according to claim 6, wherein P is a tetrahydropyranyl (THP) protecting group.

17. The process according to claim 6, wherein A is $(CH_2)_2Ph$,

- - - - - represents a double bond and P is THP.

18. The process according to claim 7, wherein P is a tetrahydropyranyl (THP) protecting group.

19. The process according to claim 7 or claim 18, wherein A is $(CH_2)_2Ph$ and

- - - - - represents a double bond.

20. The process according to claim 8, wherein P is a tetrahydropyranyl (THP) protecting group.

21. The process according to claim 8, wherein A is $(CH_2)_2Ph$, P is THP,

- - - - -

22. The process according to claim 8, wherein A is $(CH_2)_2Ph$, P is THP,

- - - - - represents a double bond, and compound (VIIb) reacts to give compound (VIb).

23. The process according to claim 8, wherein A is $(CH_2)_2Ph$,

- - - - - represents a double bond, and compound (VIIc) reacts to give compound (VIc).

24. The process according to claim 9, wherein P is a tetrahydropyranyl (THP) protecting group.

25. The process according to claim 9, wherein A is $(CH_2)_2Ph$, P is THP and compound (VIa) reacts to give compound (Va).

26. The process according to claim 9, wherein A is $(CH_2)_2Ph$, P is THP and compound (VIb) reacts to give compound (Vb).

27. The process according to claim 9, wherein A is $(CH_2)_2Ph$ and compound (VIc) reacts to give compound (Vc).

28. The process according to claim 10, wherein P is a tetrahydropyranyl (THP) protecting group.

29. The process according to claim 10, wherein A is $(CH_2)_2Ph$, P is THP,

- - - - - represents a single bond, and compound (Va) reacts to give compound (IVa).

30. The process according to claim 10, wherein A is $(CH_2)_2Ph$, P is THP,

- - - - - represents a single bond, and compound (Vb) reacts to give compound (IVb).

31. The process according to claim 10, wherein A is $(CH_2)_2Ph$,

- - - - - represents a single bond, and compound (Vc) reacts to give compound (IVc).

32. The process according to claim 11, wherein the compound having the formula (I) is Travoprost.

33. The process according to claim 4, wherein the compound having the formula (I) is Travoprost.

34. The process according to claim 4, wherein A is $CH_2CH_2$-Ph,

----- represents a double bond and P is THP, the process further comprising selectively reducing the compound of formula (VIII) to provide a compound of formula (4):

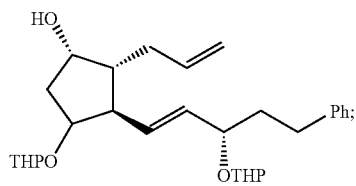
(4)

dihydroxylating the compound of formula (4) to provide a compound of formula (7):

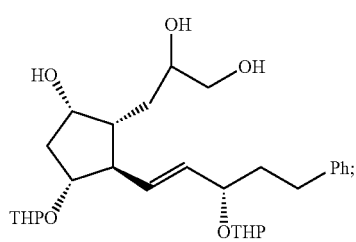
(7)

performing a diol cleavage reaction on the compound of formula (7) to provide a compound of formula (23):

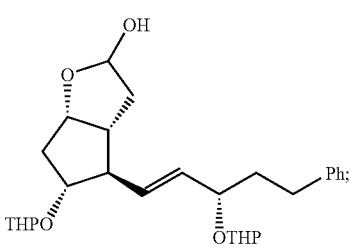
(23)

performing a Wittig reaction on the compound of formula (23) to provide a compound of formula (26):

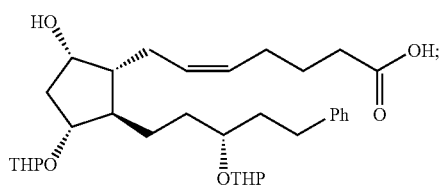
(26)

amidating the compound of formula (26) to provide a compound of formula (29):

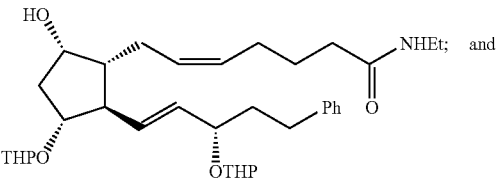
(29)

deprotecting the compound of formula (29) to provide Bimatoprost.

35. The process according to claim 4, wherein A is $CH_2CH_2$-Ph,

----- represents a double bond and P is THP, the process further comprising selectively reducing the compound of formula (VIII) to provide a compound of formula (4):

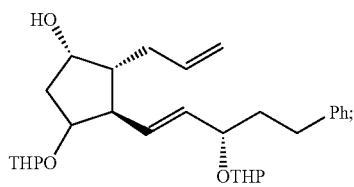
(4)

protecting the compound of formula (4) to provide a compound of formula (5):

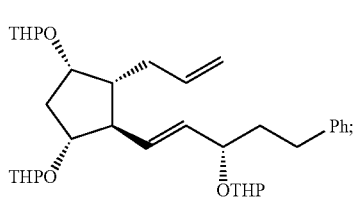
(5)

dihydroxylating the compound of formula (5) to provide a compound of formula (8):

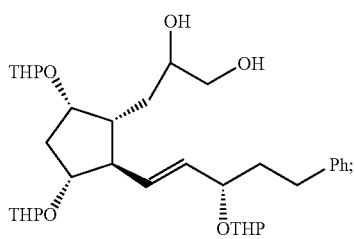
(8)

performing a diol cleavage reaction on the compound of formula (8) to provide a compound of formula (24):

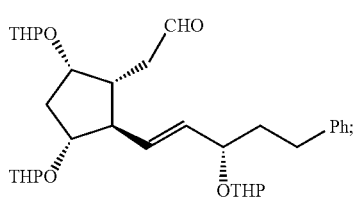
(24)

performing a Wittig reaction on the compound of formula (24) to provide a compound of formula (27):

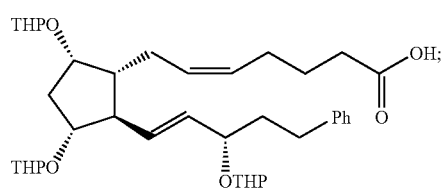
(27)

amidating the compound of formula (27) to provide a compound of formula (30):

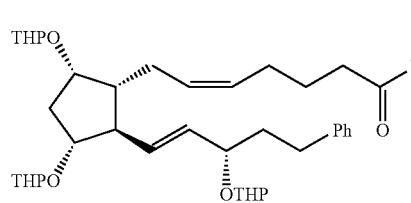
(30)

deprotecting the compound of formula (30) to provide Bimatoprost.

36. The process according to claim 4, wherein A is CH₂CH₂-Ph,

- - - - - represents a double bond and P is THP, the process further comprising selectively reducing the compound of formula (VIII) to provide a compound of formula (4):

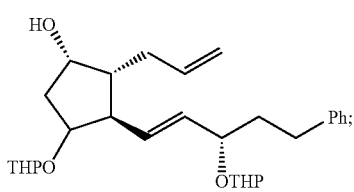
(4)

deprotecting the compound of formula (4) to provide a compound of formula (6):

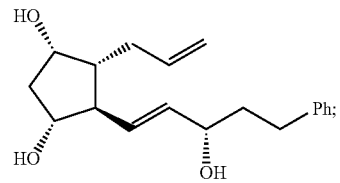
(6)

dihydroxylating the compound of formula (6) to provide a compound of formula (9):

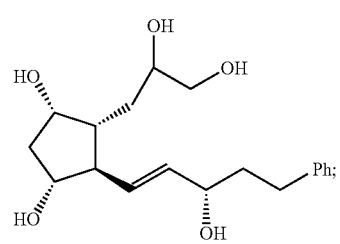
(9)

performing a diol cleavage on the compound of formula (9) to provide a compound of formula (25):

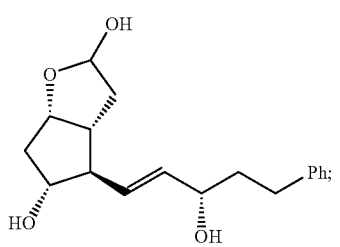
(25)

performing a Wittig reaction on the compound of formula (25) to provide a compound of formula (28):

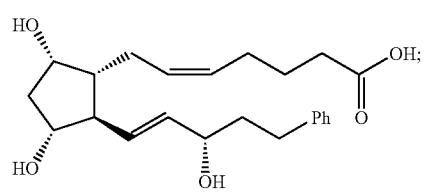
(28)

amidating the compound of formula (28) to provide Bimatoprost.

37. The process according to claim 14, wherein the compound having the formula (I) is Travoprost.

38. The process according to claim 5, wherein the compound having the formula (I) is Travoprost.

39. The process according to claim 16, wherein the compound having the formula (I) is Travoprost.

40. The process according to claim 6, wherein the compound having the formula (I) is Travoprost.

41. The process according to claim 18, wherein the compound having the formula (I) is Travoprost.

42. The process according to claim 7, wherein the compound having the formula (I) is Travoprost.

43. The process according to claim 20, wherein the compound having the formula (I) is Travoprost.

44. The process according to claim 8, wherein the compound having the formula (I) is Travoprost.

45. The process according to claim 24, wherein the compound having the formula (I) is Travoprost.

46. The process according to claim 9, wherein the compound having the formula (I) is Travoprost.

47. The process according to claim 28, wherein the compound having the formula (I) is Travoprost.

48. The process according to claim 10, wherein the compound having the formula (I) is Travoprost.

* * * * *